United States Patent
Garcia et al.

(10) Patent No.: US 9,428,567 B2
(45) Date of Patent: Aug. 30, 2016

(54) ANTAGONISTS OF INTERLEUKIN-2 RECEPTOR

(75) Inventors: Kenan Christopher Garcia, Menlo Park, CA (US); Aron Levin, New York, NY (US); Aaron Ring, Menlo Park, CA (US)

(73) Assignee: THE BOARD OF TRUSTEES OF THE LELAND STANFORD JUNIOR UNIVERSITY, Palto Alto, CA (US)

( * ) Notice: Subject to any disclaimer, the term of this patent is extended or adjusted under 35 U.S.C. 154(b) by 404 days.

(21) Appl. No.: 13/997,503

(22) PCT Filed: Dec. 22, 2011

(86) PCT No.: PCT/US2011/066911
§ 371 (c)(1),
(2), (4) Date: Oct. 10, 2013

(87) PCT Pub. No.: WO2012/088446
PCT Pub. Date: Jun. 28, 2012

(65) Prior Publication Data
US 2014/0046026 A1  Feb. 13, 2014

Related U.S. Application Data

(60) Provisional application No. 61/426,307, filed on Dec. 22, 2010.

(51) Int. Cl.
*C07K 14/55* (2006.01)
*A61K 38/00* (2006.01)

(52) U.S. Cl.
CPC *C07K 14/55* (2013.01); *A61K 38/00* (2013.01)

(58) Field of Classification Search
CPC ..................................................... C07K 14/55
See application file for complete search history.

(56) References Cited

FOREIGN PATENT DOCUMENTS

| | | |
|---|---|---|
| JP | 2002-515247 A | 5/2002 |
| WO | WO 99/60128 A1 | 11/1999 |
| WO | WO 2005/007121 A2 | 1/2005 |
| WO | WO 2006/081510 A2 | 8/2006 |
| WO | WO 2006/081510 A3 | 8/2006 |
| WO | WO 2012/119093 A1 | 9/2012 |

OTHER PUBLICATIONS

Dumont, Francis J., "Interleukin-2 family cytokines: potential for therapeutic immunoregulation," *Expert Opin. Ther. Patents*, 15:5, pp. 521-554 (2005).
Grant, et al., "The interleukin 2 receptor (IL-2R): The IL-2R α subunit alters the function of the IL-2R β subunit to enhance IL-2 binding and signaling by mechanisms that do not require binding of IL-2 to IL-2R α subunit," *Proc. Natl. Acad. Sci. USA*, vol. 89, pp. 2165-2169 (1992).
Rao et al., "Interleukin-2 mutants with enhanced α-receptor subunit binding affinity," *Protein Engineering*, 16:12, pp. 1081-1087 (2003).
Shanafelt et al., "A T-cell-selective interleukin 2 mutein exhibits potent antitumor activity and is well tolerated in vivo," *Nature Biotechnology*, vol. 18, pp. 1197-1202 (2000).
Tsudo et al., "Characterization of the interleukin 2 receptor β chain using three distinct monoclonal antibodies," *Proc. Natl. Acad. Sci. USA*, vol. 86, pp. 1982-1986 (1989).

*Primary Examiner* — Prema Mertz
(74) *Attorney, Agent, or Firm* — Morgan, Lewis & Bockius LLP; Jeffry S. Mann

(57) ABSTRACT

Novel human interleukin-2 (IL-2) muteins or variants thereof, and nucleic acid molecules and variants thereof are provided. Methods for producing these muteins as well as methods for stimulating the immune system of an animal are also disclosed. In addition, the invention provides recombinant expression vectors comprising the nucleic acid molecules of this invention and host cells into which expression vectors have been introduced. Pharmaceutical compositions are included comprising a therapeutically effective amount of a human IL-2 mutein of the invention and a pharmaceutically acceptable carrier. The IL-2 muteins can be used in pharmaceutical compositions for use in treatment of cancer and in stimulating the immune response.

18 Claims, 11 Drawing Sheets

A

First generation IL-2 library: error-prone PCR-based, tetramer selection

B

Second generation IL-2 library: hydrophobic core-directed, monomer selection

Figure 3

| residue # | 74 | 80 | 81 | 85 | 86 | 89 | 92 | 93 | $K_d$(nM) | $k_{on}$(1/ms) | $k_{off}$(1/s) |
|---|---|---|---|---|---|---|---|---|---|---|---|
| wt IL-2 | Q | L | R | L | I | I | I | V | 280 | $7.9 \times 10^5$ | 0.22 |
| 5-1 | R | | | | | | | | 235 | $3.1 \times 10^5$ | 0.073 |
| 5-2 | | | | V | | | | | 77 | $5.8 \times 10^5$ | 0.045 |
| 6-6 | | | | I | V | | | | 49 | $1.2 \times 10^6$ | 0.061 |
| A2 | H | | T | V | V | | F | I | | | |
| B1 | N | F | | V | V | V | F | | 1.6 | $3.1 \times 10^6$ | 0.005 |
| B11 | S | F | | | | | F | | | | |
| C5 | N | V | T | V | V | | F | | 10 | $1.6 \times 10^6$ | 0.016 |
| D10 | H | F | | V | V | | F | | 1.3 | $4.1 \times 10^6$ | 0.0051 |
| E10 | S | F | | V | V | | F | | 1.3 | $4.3 \times 10^6$ | 0.0055 |
| G8 | N | F | D | V | V | | F | | 1.5 | $3.2 \times 10^6$ | 0.0049 |
| H4 | S | | T | V | | | F | | 14 | $9.4 \times 10^5$ | 0.013 |
| H9 | | F | D | V | V | | F | | 1.4 | $4.1 \times 10^6$ | 0.0056 |
| CONSENSUS | | F | D | V | V | | F | | | | |

A

B (A)

(B)

(A)

(B)

SEQUENCE LISTING

```
<160> NUMBER OF SEQ ID NOS: 36

<210> SEQ ID NO 1
<211> LENGTH: 153
<212> TYPE: PRT
<213> ORGANISM: Homo sapiens

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125
```

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 3
<211> LENGTH: 169
<212> TYPE: PRT
<213> ORGANISM: Mus musculus

<400> SEQUENCE: 3

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

```
Gln Ser Ile Ile Ser Thr Ser Pro Gln
                165

<210> SEQ ID NO 4
<211> LENGTH: 149
<212> TYPE: PRT
<213> ORGANISM: Mus musculus

<400> SEQUENCE: 4

Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 5
<211> LENGTH: 133
<212> TYPE: PRT
<213> ORGANISM: Artificial Sequence
<220> FEATURE:
<223> OTHER INFORMATION: IL-2 muteins

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Arg Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

```
<210> SEQ ID NO 6
<211> LENGTH: 133
<212> TYPE: PRT
<213> ORGANISM: Artificial Sequence
<220> FEATURE:
<223> OTHER INFORMATION: IL-2 muteins

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Arg Ser Lys Asn Phe His Leu
65                  70                  75                  80

Arg Pro Arg Asp Val Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 7
<211> LENGTH: 133
<212> TYPE: PRT
<213> ORGANISM: Artificial Sequence
<220> FEATURE:
<223> OTHER INFORMATION: IL-2 muteins

<400> SEQUENCE: 7

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Arg Ser Lys Asn Phe His Leu
65                  70                  75                  80

Ile Pro Arg Asp Val Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 8
<211> LENGTH: 133
<212> TYPE: PRT
<213> ORGANISM: Artificial Sequence
```

<220> FEATURE:
<223> OTHER INFORMATION: IL-2 muteins

<400> SEQUENCE: 8

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Leu
65                  70                  75                  80

Thr Pro Arg Asp Val Val Ser Asn Ile Asn Val Phe Ile Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 9
<211> LENGTH: 133
<212> TYPE: PRT
<213> ORGANISM: Artificial Sequence
<220> FEATURE:
<223> OTHER INFORMATION: IL-2 muteins

<400> SEQUENCE: 9

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 10
<211> LENGTH: 133
<212> TYPE: PRT
<213> ORGANISM: Artificial Sequence
<220> FEATURE:
<223> OTHER INFORMATION: IL-2 muteins

<400> SEQUENCE: 10

```
Ala Pro Thr Ser Ser Ser Thr Lys Lys Thr Gln Leu Gln Leu Glu His
1               5                   10                  15

Leu Leu Leu Asp Leu Gln Met Val Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 11
<211> LENGTH: 133
<212> TYPE: PRT
<213> ORGANISM: Artificial Sequence
<220> FEATURE:
<223> OTHER INFORMATION: IL-2 muteins

<400> SEQUENCE: 11

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

His Leu Glu Glu Val Leu Asn Leu Ala Asn Ser Lys Asn Phe His Val
65                  70                  75                  80

Thr Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 12
<211> LENGTH: 133
<212> TYPE: PRT
<213> ORGANISM: Artificial Sequence
<220> FEATURE:
<223> OTHER INFORMATION: IL-2 muteins

<400> SEQUENCE: 12

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

```
Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala His Ser Lys Asn Phe His Phe
 65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 13
<211> LENGTH: 133
<212> TYPE: PRT
<213> ORGANISM: Artificial Sequence
<220> FEATURE:
<223> OTHER INFORMATION: IL-2 muteins

<400> SEQUENCE: 13

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Ser Ser Lys Asn Phe His Phe
 65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 14
<211> LENGTH: 133
<212> TYPE: PRT
<213> ORGANISM: Artificial Sequence
<220> FEATURE:
<223> OTHER INFORMATION: IL-2 muteins

<400> SEQUENCE: 14

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
```

```
                50                  55                  60
Pro Leu Glu Glu Val Leu Asn Leu Ala Asn Ser Lys Asn Phe His Phe
 65                  70                  75                  80

Asp Pro Arg Asp Val Val Ser Asn Ile Asn Val Phe Val Leu Glu Leu
                     85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 15
<211> LENGTH: 133
<212> TYPE: PRT
<213> ORGANISM: Artificial Sequence
<220> FEATURE:
<223> OTHER INFORMATION: IL-2 muteins

<400> SEQUENCE: 15

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Ser Ser Lys Asn Phe His Leu
 65                  70                  75                  80

Thr Pro Arg Asp Val Ile Ser Asn Ile Asn Val Phe Val Leu Glu Leu
                     85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 16
<211> LENGTH: 133
<212> TYPE: PRT
<213> ORGANISM: Artificial Sequence
<220> FEATURE:
<223> OTHER INFORMATION: IL-2 muteins

<400> SEQUENCE: 16

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Phe
 65                  70                  75                  80
```

```
Asp Pro Arg Asp Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 17
<211> LENGTH: 20
<212> TYPE: DNA
<213> ORGANISM: Artificial Sequence
<220> FEATURE:
<223> OTHER INFORMATION: Primer IL-2_errprone_for

<400> SEQUENCE: 17
gcacctactt caagttctac                                              20

<210> SEQ ID NO 18
<211> LENGTH: 15
<212> TYPE: DNA
<213> ORGANISM: Artificial Sequence
<220> FEATURE:
<223> OTHER INFORMATION: primer IL-2_errprone_rev

<400> SEQUENCE: 18
gccaccagag gatcc                                                   15

<210> SEQ ID NO 19
<211> LENGTH: 74
<212> TYPE: DNA
<213> ORGANISM: Artificial Sequence
<220> FEATURE:
<223> OTHER INFORMATION: primer

<400> SEQUENCE: 19
agtggtggtg gtggttctgg tggtggtggt tctggtggtg gtggttctgc tagcgcacct    60
acttcaagtt ctac                                                     74

<210> SEQ ID NO 20
<211> LENGTH: 69
<212> TYPE: DNA
<213> ORGANISM: Artificial Sequence
<220> FEATURE:
<223> OTHER INFORMATION: primer

<400> SEQUENCE: 20
acactgttgt tatcagatct cgagcaagtc ttcttcggag ataagctttt gttcgccacc    60
agaggatcc                                                           69

<210> SEQ ID NO 21
<211> LENGTH: 47
<212> TYPE: DNA
<213> ORGANISM: Artificial Sequence
<220> FEATURE:
<223> OTHER INFORMATION: IL-2_affmat_ass01

<400> SEQUENCE: 21
gcacctactt caagttctac aaagaaaaca cagctacaac tggagca                 47

<210> SEQ ID NO 22
<211> LENGTH: 47
```

-continued

<212> TYPE: DNA
<213> ORGANISM: Artificial Sequence
<220> FEATURE:
<223> OTHER INFORMATION: il-2_affmat_ass02

<400> SEQUENCE: 22
caaaatcatc tgtaaatcca gaagtaaatg ctccagttgt agctgtg        47

<210> SEQ ID NO 23
<211> LENGTH: 47
<212> TYPE: DNA
<213> ORGANISM: Artificial Sequence
<220> FEATURE:
<223> OTHER INFORMATION: il-2_affmat_ass03

<400> SEQUENCE: 23
ggatttacag atgattttga atggaattaa taattacaag aatccca        47

<210> SEQ ID NO 24
<211> LENGTH: 47
<212> TYPE: DNA
<213> ORGANISM: Artificial Sequence
<220> FEATURE:
<223> OTHER INFORMATION: il-2_affmat_ass04b

<400> SEQUENCE: 24
aacttagctg tgagcatcct ggtgagtttg ggattcttgt aattatt        47

<210> SEQ ID NO 25
<211> LENGTH: 47
<212> TYPE: DNA
<213> ORGANISM: Artificial Sequence
<220> FEATURE:
<223> OTHER INFORMATION: il-2_affmat_ass05b

<400> SEQUENCE: 25
ggatgctcac agctaagttt tacatgccca agaaggccac agaactg        47

<210> SEQ ID NO 26
<211> LENGTH: 47
<212> TYPE: DNA
<213> ORGANISM: Artificial Sequence
<220> FEATURE:
<223> OTHER INFORMATION: il-2_affmat_ass06

<400> SEQUENCE: 26
gttcttcttc tagacactga agatgtttca gttctgtggc cttcttg        47

<210> SEQ ID NO 27
<211> LENGTH: 48
<212> TYPE: DNA
<213> ORGANISM: Artificial Sequence
<220> FEATURE:
<223> OTHER INFORMATION: il-2_affmat_ass07

<400> SEQUENCE: 27
cagtgtctag aagaagaact caaacctctg gaggaagtgc taaattta       48

<210> SEQ ID NO 28
<211> LENGTH: 40
<212> TYPE: DNA
<213> ORGANISM: Artificial Sequence
<220> FEATURE:
<223> OTHER INFORMATION: il-2_affmat_ass08

<400> SEQUENCE: 28
gtgaaagttt ttgctsykag ctaaatttag cacttcctcc                                40

<210> SEQ ID NO 29
<211> LENGTH: 74
<212> TYPE: DNA
<213> ORGANISM: Artificial Sequence
<220> FEATURE:
<223> OTHER INFORMATION: il-2_affmat_ass09
<220> FEATURE:
<221> NAME/KEY: misc_feature
<222> LOCATION: (16)..(16)
<223> OTHER INFORMATION: N is any one of adenine, thymine, guanine or
      cytosine nucleotides
<220> FEATURE:
<221> NAME/KEY: misc_feature
<222> LOCATION: (19)..(20)
<223> OTHER INFORMATION: N is any one of adenine, thymine, guanine or
      cytosine nucleotides
<220> FEATURE:
<221> NAME/KEY: misc_feature
<222> LOCATION: (21)..(21)
<223> OTHER INFORMATION: K is either guanine or thymine
<220> FEATURE:
<221> NAME/KEY: misc_feature
<222> LOCATION: (31)..(31)
<223> OTHER INFORMATION: N is any one of adenine, thymine, guanine or
      cytosine nucleotides
<220> FEATURE:
<221> NAME/KEY: misc_feature
<222> LOCATION: (34)..(34)
<223> OTHER INFORMATION: N is any one of adenine, thymine, guanine or
      cytosine nucleotides
<220> FEATURE:
<221> NAME/KEY: misc_feature
<222> LOCATION: (43)..(43)
<223> OTHER INFORMATION: N is any one of adenine, thymine, guanine or
      cytosine nucleotides
<220> FEATURE:
<221> NAME/KEY: misc_feature
<222> LOCATION: (52)..(52)
<223> OTHER INFORMATION: N is any one of adenine, thymine, guanine or
      cytosine nucleotides
<220> FEATURE:
<221> NAME/KEY: misc_feature
<222> LOCATION: (55)..(55)
<223> OTHER INFORMATION: N is any one of adenine, thymine, guanine or
      cytosine nucleotides

<400> SEQUENCE: 29
agcaaaaact ttcacntcnn kcccagggac ntcntcagca atntcaacgt antcntcctg          60
gaactaaagg gatc                                                            74

<210> SEQ ID NO 30
<211> LENGTH: 49
<212> TYPE: DNA
<213> ORGANISM: Artificial Sequence
<220> FEATURE:
<223> OTHER INFORMATION: il-2_affmat_ass10

<400> SEQUENCE: 30
catcagcata ttcacacatg aatgttgttt cagatcccct tagttccag                     49

<210> SEQ ID NO 31
<211> LENGTH: 49
<212> TYPE: DNA
<213> ORGANISM: Artificial Sequence
<220> FEATURE:
<223> OTHER INFORMATION: il-2_affmat_ass11

<400> SEQUENCE: 31
atgtgtgaat atgctgatga gacagcaacc attgtagaat ttctgaaca                     49

```
<210> SEQ ID NO 32
<211> LENGTH: 49
<212> TYPE: DNA
<213> ORGANISM: Artificial Sequence
<220> FEATURE:
<223> OTHER INFORMATION: il-2_affmat_ass12

<400> SEQUENCE: 32
agatgatgct tgacaaaag gtaatccatc tgttcagaaa ttctacaat              49

<210> SEQ ID NO 33
<211> LENGTH: 45
<212> TYPE: DNA
<213> ORGANISM: Artificial Sequence
<220> FEATURE:
<223> OTHER INFORMATION: il-2_affmat_ass13

<400> SEQUENCE: 33
ttttgtcaaa gcatcatctc aacactaact ggatcctctg gtggc                 45

<210> SEQ ID NO 34
<211> LENGTH: 74
<212> TYPE: DNA
<213> ORGANISM: Artificial Sequence
<220> FEATURE:
<223> OTHER INFORMATION: PCR amplification oligos il-2_site2_assfor

<400> SEQUENCE: 34
agtggtggtg gtggttctgg tggtggtggt tctggtggtg gtggttctgc tagcgcacct   60
acttcaagtt ctac                                                    74

<210> SEQ ID NO 35
<211> LENGTH: 69
<212> TYPE: DNA
<213> ORGANISM: Artificial Sequence
<220> FEATURE:
<223> OTHER INFORMATION: PCR amplification oligos il-2_site2_assrev

<400> SEQUENCE: 35
acactgttgt tatcagatct cgagcaagtc ttcttcggag ataagctttt gttcgccacc   60
agaggatcc                                                          69

<210> SEQ ID NO 36
<211> LENGTH: 14
<212> TYPE: PRT
<213> ORGANISM: Artificial Sequence
<220> FEATURE:
<223> OTHER INFORMATION: biotin acceptor peptide

<400> SEQUENCE: 36

Leu Asn Asp Ile Phe Glu Ala Gln Lys Ile Glu Trp His Glu
1               5                   10
```

ANTAGONISTS OF INTERLEUKIN-2 RECEPTOR

This application is a 371 National Phase application of PCT/US2011/066911 filed Dec. 22, 2011 which claims priority to U.S. Provisional Application No. 61/426,307 filed on Dec. 22, 2010, both of which are incorporated herein by reference in their entireties.

BACKGROUND

Interleukin 2 (IL-2) is a pluripotent cytokine produced primarily by activated CD4$^+$ T cells, which plays a crucial role in producing a normal immune response. IL-2 promotes proliferation and expansion of activated T lymphocytes, potentiates B cell growth, and activates monocytes and natural killer cells. It was by virtue of these activities that IL-2 was tested and is used as an approved treatment of cancer (aldesleukin, Proleukin®).

In eukaryotic cells human IL-2 is synthesized as a precursor polypeptide of 153 amino acids, from which 20 amino acids are removed to generate mature secreted IL-2 (Taniguchi 1983). Recombinant human IL-2 has been produced in *E. coli* (Rosenberg 1984), in insect cells (Smith 1985) and in mammalian COS cells (Taniguchi 1983).

IL-2 works by interacting with three different receptors: the interleukin 2 receptor alpha (IL-2Rα; CD25), the interleukin 2 receptor beta (IL-2Rβ; CD122), and the interleukin 2 receptor gamma (IL-2Rγ; CD132; common gamma chain). The first receptor to be identified was the IL-2Rα, which is a 55 kD polypeptide (p55) that appears upon T cell activation and was originally called Tac (for T activation) antigen. The IL-2Rα binds IL-2 with a $K_d$ of approximately $10^{-8}$ M, and is also known as the "low affinity" IL-2 receptor. Binding of IL-2 to cells expressing only the IL-2Rα does not lead to any detectable biologic response.

The IL-2Rβ is a member of the type I cytokine receptor family characterized by the two cysteine/WSXWS motif. The IL-2Rβ is expressed coordinately with the IL-2Rγ. The IL-2Rγ, a 64 kD polypeptide, is also known as the common γ chain because it is shared among a number of cytokine receptors, including the receptor for interleukin-4 and interleukin-7. The IL-2Rβγ is the same signaling receptor complex that can bind to IL-15.

Most cells, for example, resting T cells are insensitive to IL-2 since they only express the IL-2Rβ and the IL-2Rγ. Upon antigen receptor-mediated T cell activation, the IL-2Rα is rapidly expressed. Once the IL-2Rα binds IL-2, it then sequentially engages the IL-2Rβ and the IL-2Rγ (FIG. 1). IL-2 binding by the IL-2Rαβγ complex results in signal transduction through a Jak/STAT signaling pathway and IL-2 mediated growth stimulation.

So far, only limited structure/function analysis of human IL-2 has occurred, although analysis of mouse IL-2 has been extensive (Zurawski, S. M. and Zurawski, (1989) *Embo J* 8: 2583-90; Zurawski, S. M, et. al., (1990) *Embo J* 9: 3899-905; Zurawski, G. (1991). *Trends Biotechnol* 9: 250-7; Zurawski, S. M. and Zurawski, G. (1992) *Embo J* 11: 3905-10. Zurawski, et. al., *EMBO J*, 12 5113-5119 (1993)). Some human IL-2 muteins have been examined for their activity on human PHA blasts (Xu, et. al., *Eur. Cytokine Netw*, 6, 237-244 (1995)). Other examples of human IL-2 muteins are provided by Buchli and Ciardelli, *Arch. Biochem. Biophys*, 307(2): 411-415, (1993), Collins, L., et al., *PNAS USA* 85:7709-7713 (1988), and U.S. Pat. No. 5,696,234 (Zurawski et al.).

The use of IL-2 as an antineoplastic agent has been limited by the serious toxicities that accompany the doses necessary for a tumor response. The major side effect of IL-2 therapy is vascular leak syndrome (VLS), which leads to the accumulation of intravascular fluid in the lungs and liver resulting in pulmonary edema and liver damage. Until recently it was believed that VLS was caused by the release of proinflammatory cytokines from IL-2 activated NK cells. However, a recent report points to the direct binding of IL-2 to lung endothelial cells, as a purported cause of VLS. (Krieg et al., *PNAS USA* 107(26)11906-11911 (2010). In principle, an IL-2 variant with high affinity for IL-2Rβ, whose activity was not dependent on CD25 expression could have improved clinical utility and reduced toxicity.

One IL-2 mutein of clinical interest is BAY 50-4798, which differs from wild-type IL-2 by the substitution of arginine for asparagine at position 88 (R88N) (Steppan et al. (2006) *J. Interferon and Cytokine Res.*, 26(3): 171-. This modification allegedly results in an IL-2 mutein with relatively reduced binding to the IL-2Rβγ, and thought to possess lower toxicity relative to wild type IL-2. However, a clinical study found that patients receiving BAY 50-4798 experienced a similar degree of IL-2 mediated VLS.

For these reasons, it is clear that IL-2 muteins that exhibit unique properties are needed. Potential uses of such muteins include treating cancer (as a direct and/or adjunct therapy) and immunodeficiency (e.g., HIV and tuberculosis). Other potential uses of IL-2 are derived from its immunostimulatory activity, and include direct treatment of cancer, treating immunodeficiency, such as HIV or human SCID patients; treating infectious disease, such as tuberculosis; its use as an adjuvant in "cancer vaccine" strategies; and for immune system stimulation indications, such as enhancing standard vaccination protocols (e.g., elderly). For example, IL-2 muteins that exhibit reduced VLS would be advantageous.

The present disclosure provides novel IL-2 muteins.

SUMMARY OF THE INVENTION

IL-2 exerts a wide spectrum of effects on the immune system, and it plays crucial roles in regulating both immune activation and homeostasis. As an immune system stimulator, IL-2 has found use in the treatment of cancer and chronic viral infections. The stimulatory affects of IL-2 can also cause havoc, mediating autoimmunity and transplant rejection. Because of its instrumental role in immune regulation and disease, the identification of IL-2 molecules with improved qualities remains an active area of research.

To these ends, the instant disclosure provides novel IL-2 compositions based on new insights into how IL-2 interacts with its cognate receptors. In most circumstances, IL-2 works through three different receptors: the IL-2Rα, the IL-2Rβ, and the IL-2Rγ. Most cells, such as resting T cells, are not responsive to IL-2 since they only express the IL-2Rβ, and the IL-2Rγ, which have low affinity for IL-2. Upon stimulation, resting T cells express the relatively high affinity IL-2 receptor IL-2Rα. Binding of IL-2 to the IL-2Rα causes this receptor to sequentially engage the IL-2Rβ, and the IL-2Rγ, bringing about T cell activation.

Based on a structural analysis of the interaction of IL-2 with its receptors, mutant forms of IL-2 were made which possess relatively increased affinity for the IL-2 Rβ when compared to wild-type IL-2, such that IL-2 mediated stimulation no longer requires engagement of the IL-2Rα. Such mutants are potent IL-2 signaling agonists.

Thus, in one embodiment an IL-2Rβ binding protein is disclosed, wherein the equilibrium dissociation constant for the IL-2Rβ is less than that of wild-type human IL-2.

Using these novel "super"-agonist IL-2 molecules as a starting point, "super"-antagonists were made which can bind IL-2Rβ, reducing the interaction of IL-2Rβ with IL-2Rγ and receptor signaling.

In other embodiments, a method for producing an IL-2Rβ binding protein is described, the method encompassing mutating a human IL-2, producing a first generation IL-2 mutein, identifying a first generation IL-2 mutein with an equilibrium dissociation constant for an interleukin-2 receptor β less than that of wild-type human IL-2, mutating the identified first generation IL-2 mutein, producing a second generation IL-2 mutein, identifying a second generation IL-2 mutein which binds and/or signals through an interleukin-2 receptor γ relatively less than wild-type IL2, thereby generating an IL-2 binding protein.

Collectively, these IL-2 muteins are referred to as "super-2s."

BRIEF DESCRIPTION OF THE DRAWINGS

FIG. 3: Depicts the amino acid residues altered in the IL-2 muteins shown relative to the wild-type IL-2 sequence. The binding affinity of each mutein and IL-2 for the IL-2Rβ is also shown.

DETAILED DESCRIPTION

Figure 1:
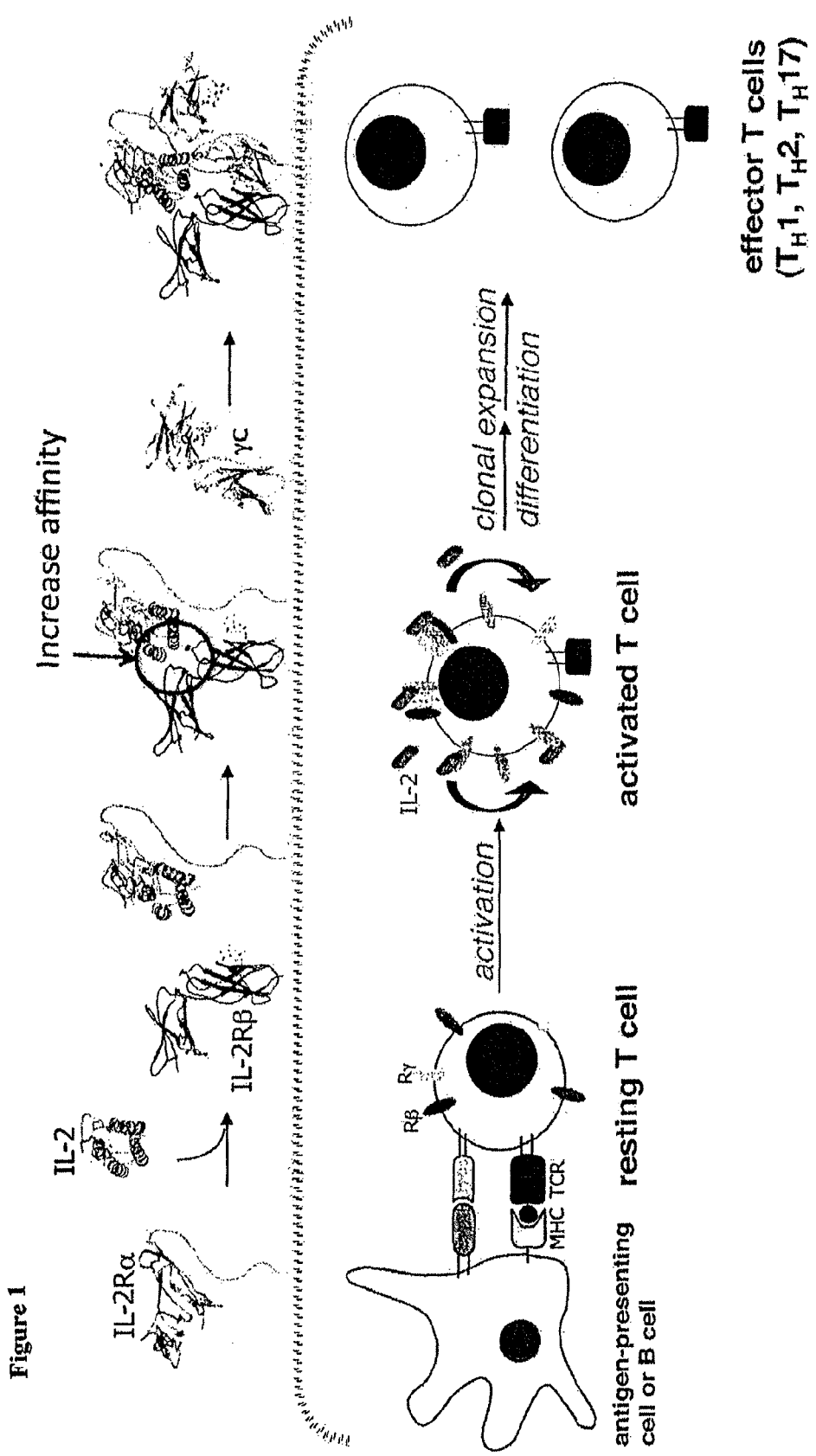
FIG. 1: Schematic representation of the interaction of IL-2 with its receptors and affects on T cells. The binding of IL-2 by the IL-2Rα results in the sequential engagement of the IL-2Rβ and the IL-2Rγ. IL-2 causes T cell clonal expansion and differentiation.

In order for the present disclosure to be more readily understood, certain terms and phrases are defined below as well as throughout the specification.

Definitions

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); and Sambrook and Russell, *Molecular Cloning: A Laboratory Manual* 3rd ed., Cold Spring harbor Laboratory Press (Cold Spring Harbor, N.Y. 2001), provide one skilled in the art with a general guide to many terms used in the present disclosure. As appropriate, procedures involving the use of commercially available kits and reagents are generally carried out in accordance with manufacturer defined protocols and/or parameters unless otherwise noted.

As used herein, "IL-2" means wild-type IL-2, whether native or recombinant. Mature human IL-2 occurs as a 133 amino acid sequence (less the signal peptide, consisting of an additional 20 N-terminal amino acids), as described in Fujita, et. al., PNAS USA, 80, 7437-7441 (1983). The amino acid sequence of human IL-2 (SEQ ID NO: 1) is found in Genbank under accession locator NP_000577.2. The amino acid sequence of mature human IL-2 is depicted in SEQ ID NO: 2. The murine (*Mus musculus*) IL-2 amino acid sequence is found in Genbank under accession locator (SEQ ID NO: 3). The amino acid sequence of mature murine IL-2 is depicted in SEQ ID NO: 4.

"Numbered in accordance with IL-2" means identifying a chosen amino acid with reference to the position at which that amino acid normally occurs in the mature sequence of wild type IL-2, for example R81 refers to the eighty-first amino acid, arginine, that occurs in SEQ ID NO: 2.

The term "cell types having the IL-2Rαβγ receptor" means the cells known to have this receptor type, i.e., T cells, activated T cells, B cells, activated monocytes, and activated NK cells. The term "cell types having the IL-2Rβγ receptor" means the cells known to have that receptor type, i.e., B cells, resting monocytes, and resting NK cells.

The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match

```
                                                      SEQ ID NO: 1
MYRMQLLSCIALSLALVTNSAPTSSSTKKTQLQLEHLLLDLQMILNGINNYKNPKLTRM

LTFKFYMPKKATELKHLQCLEEELKPLEEVLNLAQSKNFHLRPRDLISNINVIVLELKGSE

TTFMCEYADETATIVEFLNRWITFCQSIISTLT

SEQ ID NO: 2
APTSSSTKKTQLQLEHLLLDLQMILNGINNYKNPKLTRMLTFKFYMPKKATELKHLQCL

EEELKPLEEVLNLAQSKNFHLRPRDLISNINVIVLELKGSETTFMCEYADETATIVEFLNR

WITFCQSIISTLT

SEQ ID NO: 3
MYSMQLASCVTLTLVLLVNSAPTSSSTSSSTAEAQQQQQQQQQQQQQHLEQLLMDLQEL

LSRMENYRNLKLPRMLTFKFYLPKQATELKDLQCLEDELGPLRHVLDLTQSKSFQLEDA

ENFISNIRVTVVKLKGSDNTFECQFDDESATVVDFLRRWIAFCQSIISTSPQ

SEQ ID NO: 4
APTSSSTSSSTAEAQQQQQQQQQQQQQHLEQLLMDLQELLSRMENYRNLKLPRMLTFKF

YLPKQATELKDLQCLEDELGPLRHVLDLTQSKSFQLEDAENFISNIRVTVVKLKGSDNTF

ECQFDDESATVVDFLRRWIAFCQSIISTSPQ
```

As used herein, "IL-2 mutein" means a polypeptide wherein specific substitutions to the interleukin-2 protein have been made. FIG. 3, for example, discloses twelve IL-2 muteins and their corresponding relative binding affinity for the IL-2Rβ. The IL-2 muteins can also be characterized by amino acid insertions, deletions, substitutions and modifications at one or more sites in or at the other residues of the native IL-2 polypeptide chain. In accordance with this disclosure any such insertions, deletions, substitutions and modifications result in an IL-2 mutein that retains the IL-2Rβ binding activity. Exemplary muteins can include substitutions of 1, 2, 3, 4, 5, 6, 7, 8, 9, 10 or more amino acids.

Muteins also include conservative modifications and substitutions at other positions of IL-2 (i.e., those that have a minimal effect on the secondary or tertiary structure of the mutein). Such conservative substitutions include those described by Dayhoff in *The Atlas of Protein Sequence and Structure* 5 (1978), and by Argos in *EMBO J.*, 8:779-785 (1989). For example, amino acids belonging to one of the following groups represent conservative changes: Group I: ala, pro, gly, gln, asn, ser, thr; Group II: cys, ser, tyr, thr; Group III: val, ile, leu, met, ala, phe; Group IV: lys, arg, his; Group V: phe, tyr, trp, his; and Group VI: asp, glu.

is obtained. If necessary, identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The term "polypeptide," "protein" or "peptide" refer to any chain of amino acid residues, regardless of its length or post-translational modification (e.g., glycosylation or phosphorylation).

In the event the mutant IL-2 polypeptides of the disclosure are "substantially pure," they can be at least about 60% by weight (dry weight) the polypeptide of interest, for example, a polypeptide containing the mutant IL-2 amino acid sequence. For example, the polypeptide can be at least about 75%, about 80%, about 85%, about 90%, about 95% or about 99%, by weight, the polypeptide of interest. Purity can be measured by any appropriate standard method, for example, column chromatography, polyacrylamide gel electrophoresis, or HPLC analysis.

"Operably linked" is intended to mean that the nucleotide sequence of interest (i.e., a sequence encoding an IL-2 mutein) is linked to the regulatory sequence(s) in a manner that allows for expression of the nucleotide sequence (e.g., in an in vitro transcription/translation system or in a host cell when the vector is introduced into the host cell). "Regulatory sequences" include promoters, enhancers, and other expression control elements (e.g., polyadenylation signals). See, for example, Goeddel (1990) in Gene Expression Technology: Methods in Enzymology 185 (Academic Press, San Diego, Calif.). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression constructs of the invention can be introduced into host cells to thereby produce the human IL-2 muteins disclosed herein or to produce biologically active variants thereof.

The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell but are still included within the scope of the term as used herein.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, particle gun, or electroporation.

As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions.

As used herein, we may use the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. The terms "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. An "adenocarcinoma" refers to a carcinoma derived from glandular tissue or in which the tumor cells form recognizable glandular structures.

As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

IL-2 Muteins

In various embodiments, the present disclosure provides IL-2 polypeptides, which may be, but are not necessarily, substantially purified and that can function as an agonist of wild-type IL-2; carrying out one or more of the biological activities of IL-2 (e.g., stimulation of cellular proliferation)). IL-2 has been characterized as a T cell growth factor that induces proliferation of antigen-activated T cells and stimulation of NK cells.

Also, described are IL-2 polypeptides that can function as an antagonist of wild-type IL-2; that is, preventing the biological activity of IL-2.

An exemplary mutant IL-2 polypeptide includes an amino acid sequence that is at least about 80% identical to SEQ ID NO:2 which binds the IL-2Rβ with an affinity that is greater than the affinity with which the polypeptide represented by SEQ ID NO: 2 binds the IL-2Rβ. For example, a mutant IL-2 polypeptide can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-2, and that binds the IL-2Rβ with higher affinity than a wild-type IL-2.

An exemplary mutant IL-2 polypeptide can also include an amino acid sequence that is at least about 80% identical to SEQ ID NO: 2 and that binds to an IL-2 receptor γ (IL-2Rγ) with an affinity that is less than the affinity with which the polypeptide represented by SEQ ID NO: 2 binds the IL-2Rγ. For example, a mutant IL-2 polypeptide can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-2, and that binds the IL-2Rγ with lower affinity than a wild-type IL-2.

Exemplary mutant IL-2 polypeptides can be at least about 50%, at least about 65%, at least about 70%, at least about 80%, at least about 85%, at least about 87%, at least about 90%, at least about 95%, at least about 97%, at least about 98%, or at least about 99% identical to wild-type IL-2. The mutation can consist of a change in the number or content of amino acid residues. For example, the mutant IL-2 can have a greater or a lesser number of amino acid residues than wild-type IL-2. Alternatively, or in addition, an exemplary mutant polypeptide can contain a substitution of one or more amino acid residues that are present in the wild-type IL-2. In various embodiments, the mutant IL-2 polypeptide can differ from wild-type IL-2 by the addition, deletion, or substitution of a single amino acid residue, for example, a substitution of the residue at position 69. Similarly, exemplary mutant polypeptides can differ from wild-type by a substitution of two amino acid residues, for example, the residues at positions 24, 65, 74, 80, 81, 85, 86, 89, 92, and 93 of SEQ ID NO:2.

By way of illustration, a polypeptide that includes an amino acid sequence that is at least 95% identical to a reference amino acid sequence of SEQ ID NO:2 is a polypeptide that includes a sequence that is identical to the reference sequence except for the inclusion of up to five alterations of the reference amino acid of SEQ ID NO: 2. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence can occur at the amino (N—) or carboxy (C—) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. These mutations can be at amino acid residues that contact the IL-2Rβ and/or the IL-2Rγ.

More specifically, a mutation (whether conservative or non-conservative, by way of addition(s) or deletion(s)) can be made at one or more of positions. For example, the mutation can be: I24V, P65H, Q74R, Q74 H, Q74N, Q74S, L80F, L80V, R81I, R81T, R81D, L85V, I86V, I89V, I92F, V93I. The sequences of exemplary IL-2 muteins are as follows: 5-1 SEQ ID NO: 5; 5-2 SEQ ID NO: 6; 6-6 SEQ ID NO: 7; A2 SEQ ID NO: 8; B1 SEQ ID NO: 9; B11 SEQ ID NO: 10; C5 SEQ ID NO: 11; D10 SEQ ID NO: 12; E10 SEQ ID NO: 13; G8 SEQ ID NO: 14; H4 SEQ ID NO: 15; and H9 SEQ ID NO: 16.

```
                                                          SEQ ID NO: 5
APTSSSTKKTQLQLEHLLLDLQMILNGINNYKNPKLTRMLTFKFYMPKKATELKHLQCL

EEELKPLEEVLNLARSKNFHLRPRDLISNINVIVLELKGSETTFMCEYADETATIVEFLNR

WITFCQSIISTLT

SEQ ID NO: 6
APTSSSTKKTQLQLEHLLLDLQMILNGINNYKNPKLTRMLTFKFYMPKKATELKHLQCL

EEELKPLEEVLNLARSKNFHLRPRDVISNINVIVLELKGSETTFMCEYADETATIVEFLNR

WITFCQSIISTLT

SEQ ID NO: 7
APTSSSTKKTQLQLEHLLLDLQMILNGINNYKNPKLTRMLTFKFYMPKKATELKHLQCL

EEELKPLEEVLNLARSKNFHLIPRDVISNINVIVLELKGSETTFMCEYADETATIVEFLNR

WITFCQSIISTLT

SEQ ID NO: 8
APTSSSTKKTQLQLEHLLLDLQMILNGINNYKNPKLTRMLTFKFYMPKKATELKHLQCL

EEELKPLEEVLNLAHSKNFHLTPRDVVSNINVFILELKGSETTFMCEYADETATIVEFLN

RWITFCQSIISTLT

SEQ ID NO: 9
APTSSSTKKTQLQLEHLLLDLQMILNGINNYKNPKLTRMLTFKFYMPKKATELKHLQCL

EEELKPLEEVLNLANSKNFHFDPRDVVSNVNVFVLELKGSETTFMCEYADETATIVEFL

NRWITFCQSIISTLT

SEQ ID NO: 10
APTSSSTKKTQLQLEHLLLDLQMVLNGINNYKNPKLTRMLTFKFYMPKKATELKHLQC

LEEELKPLEEVLNLASSKNFHFDPRDVVSNINVFVLELKGSETTFMCEYADETATIVEFL

NRWITFCQSIISTLT
```

-continued

SEQ ID NO: 11

APTSSSTKKTQLQLEHLLLDLQMILNGINNYKNPKLTRMLTFKFYMPKKATELKHLQCL

EEELKHLEEVLNLANSKNFHVTPRDVVSNINVFVLELKGSETTFMCEYADETATIVEFLN

RWITFCQSIISTLT

SEQ ID NO: 12
APTSSSTKKTQLQLEHLLLDLQMILNGINNYKNPKLTRMLTFKFYMPKKATELKHLQCL

EEELKPLEEVLNLAHSKNFHFDPRDVVSNINVFVLELKGSETTFMCEYADETATIVEFLN

RWITFCQSIISTLT

SEQ ID NO: 13
APTSSSTKKTQLQLEHLLLDLQMILNGINNYKNPKLTRMLTFKFYMPKKATELKHLQCL

EEELKPLEEVLNLASSKNFHFDPRDVVSNINVFVLELKGSETTFMCEYADETATIVEFLN

RWITFCQSIISTLT

SEQ ID NO: 14
APTSSSTKKTQLQLEHLLLDLQMILNGINNYKNPKLTRMLTFKFYMPKKATELKHLQCL

EEELKPLEEVLNLANSKNFHFDPRDVVSNINVFVLELKGSETTFMCEYADETATIVEFLN

RWITFCQSIISTLT

SEQ ID NO: 15
APTSSSTKKTQLQLEHLLLDLQMILNGINNYKNPKLTRMLTFKFYMPKKATELKHLQCL

EEELKPLEEVLNLASSKNFHLTPRDVISNINVFVLELKGSETTFMCEYADETATIVEFLNR

WITFCQSIISTLT

SEQ ID NO: 16
APTSSSTKKTQLQLEHLLLDLQMILNGINNYKNPKLTRMLTFKFYMPKKATELKHLQCL

EEELKPLEEVLNLAQSKNFHFDPRDVVSNINVFVLELKGSETTFMCEYADETATIVEFLN

RWITFCQSIISTLT

With respect to affinity, this there are disclosed herein exemplary mutant IL-2 polypeptides that bind the IL-2Rβ with an affinity that is higher than the wild type IL-2 polypeptide by at least about 2%, at least about 5%, at least about 10%, at least about 20%, at least about 30%, or at least about 40% higher affinity or more. The wild-type IL-2 polypeptide binds the IL-2Rβ with a $K_d$ of about 280 nM. The binding affinity of exemplary disclosed mutant IL-2 polypeptides can also be expressed as 1.2, 1.4, 1.5, 2, 5, 10, 15, 20, 25, 50, 100, 200, 250 or more fold higher affinity for the IL-2Rβ than wild-type IL-2.

Alternatively, or in addition, an exemplary mutant IL-2 polypeptide can have increased potency in a T cell proliferation assay relative to wild-type IL-2. The ability of a mutant IL-2 polypeptide to bind the IL-2Rβ can be assessed by numerous assays, including the cell binding and proliferation assays described herein.

Exemplary mutant IL-2 polypeptides can have the ability to exhibit a decreased dissociation rate from the IL-2Rβ receptor subunit, such that signaling from the receptor/ligand complex persists for a longer time period following transient exposure to the mutant IL-2 polypeptide, as compared to a wild-type IL-2.

Also provided in the instant disclosure are mutant polypeptides that disrupt the association of the IL-2Rβ with the IL-2Rγ such that this interaction is reduced by about 2%, about 5%, about 10%, about 15%, about 20%, about 50%, about 75%, about 90%, about 95% or more relative to wild-type IL-2.

Exemplary mutant IL-2 polypeptides possessing both properties of increased affinity for the IL-2Rβ and disruption of the IL-2Rβ with the IL-2Rγ interaction are also disclosed.

As described further below, an exemplary class of mutant IL-2 polypeptides is provided in the instant disclosure with increased binding affinity for the IL-2Rβ and/or decreased binding affinity to the IL-2Rγ using yeast surface display relative to wild-type IL-2.

Structural Comparison of IL-2 Muteins with Wild-Type IL-2

Recombinant Expression of IL-2 Muteins, Expression Vectors and Host Cells

In various embodiments, polypeptides used in the practice of the instant invention are synthetic, or are produced by expression of a recombinant nucleic acid molecule. In the event the polypeptide is a chimera (e.g., a fusion protein containing at least a mutant IL-2 polypeptide and a heterologous polypeptide), it can be encoded by a hybrid nucleic acid molecule containing one sequence that encodes all or part of the mutant IL-2, and a second sequence that encodes all or part of the heterologous polypeptide. For example, the mutant IL-2 polypeptide may be fused to a hexa-histidine tag to facilitate purification of bacterially expressed protein, or to a hemagglutinin tag to facilitate purification of protein expressed in eukaryotic cells.

Methods for constructing a DNA sequence encoding the IL-2 muteins and expressing those sequences in a suitably transformed host include, but are not limited to, using a PCR-assisted mutagenesis technique. Mutations that consist of deletions or additions of amino acid residues to an IL-2 polypeptide can also be made with standard recombinant techniques. In the event of a deletion or addition, the nucleic acid molecule encoding IL-2 is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

The complete amino acid sequence can be used to construct a back-translated gene. A DNA oligomer containing a nucleotide sequence coding for IL-2 mutein can be synthesized. For example, several small oligonucleotides coding for portions of the desired polypeptide can be synthesized and then ligated. The individual oligonucleotides typically contain 5' or 3' overhangs for complementary assembly.

In addition to generating mutant polypeptides via expression of nucleic acid molecules that have been altered by recombinant molecular biological techniques, mutant polypeptides can be chemically synthesized. Chemically synthesized polypeptides are routinely generated by those of skill in the art.

Once assembled (by synthesis, site-directed mutagenesis or another method), the DNA sequences encoding an IL-2 mutein will be inserted into an expression vector and operatively linked to an expression control sequence appropriate for expression of the IL-2 mutein in the desired transformed host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The DNA sequence encoding the IL-2 mutein, whether prepared by site directed mutagenesis, chemical synthesis or other methods, can also include DNA sequences that encode a signal sequence. Such signal sequence, if present, should be one recognized by the cell chosen for expression of the IL-2 mutein. It can be prokaryotic, eukaryotic or a combination of the two. It can also be the signal sequence of native IL-2. The inclusion of a signal sequence depends on whether it is desired to secrete the IL-2 mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IL-2 signal sequence be used.

IL-2 Mutein Fusion Proteins

As noted above, exemplary mutant IL-2 polypeptides can be prepared as fusion or chimeric polypeptides that include a mutant IL-2 polypeptide and a heterologous polypeptide (i.e., a polypeptide that is not IL-2 or a mutant thereof) (see, e.g., U.S. Pat. No. 6,451,308). Exemplary heterologous polypeptides can increase the circulating half-life of the chimeric polypeptide in vivo, and may, therefore, further enhance the properties of the mutant IL-2 polypeptides. In various embodiments, the polypeptide that increases the circulating half-life may be a serum albumin, such as human serum albumin, or the Fc region of the IgG subclass of antibodies that lacks the IgG heavy chain variable region. Exemplary Fc regions can include a mutation that inhibits complement fixation and Fc receptor binding, or it may be lytic, i.e., able to bind complement or to lyse cells via another mechanism, such as antibody-dependent complement lysis (ADCC; U.S. Ser. No. 08/355,502 filed Dec. 12, 1994).

The "Fc region" can be a naturally occurring or synthetic polypeptide that is homologous to the IgG C-terminal domain produced by digestion of IgG with papain. IgG Fc has a molecular weight of approximately 50 kDa. The mutant IL-2 polypeptides can include the entire Fc region, or a smaller portion that retains the ability to extend the circulating half-life of a chimeric polypeptide of which it is a part. In addition, full-length or fragmented Fc regions can be variants of the wild-type molecule. That is, they can contain mutations that may or may not affect the function of the polypeptides; as described further below, native activity is not necessary or desired in all cases.

The Fc region can be "lytic" or "non-lytic," but is typically non-lytic. A non-lytic Fc region typically lacks a high affinity Fc receptor binding site and a C'1q binding site. The high affinity Fc receptor binding site of murine IgG Fc includes the Leu residue at position 235 of IgG Fc. Thus, the Fc receptor binding site can be destroyed by mutating or deleting Leu 235. For example, substitution of Glu for Leu 235 inhibits the ability of the Fc region to bind the high affinity Fc receptor. The murine C'1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fc receptor binding site and a C'1q binding site. The high affinity Fc receptor binding site includes the Leu residue at position 235 of IgG Fc, and the C'1q binding site includes the Glu 318, Lys 320, and Lys 322 residues of IgG1. Lytic IgG Fc has wild-type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., The Immunologist 2:119-124, 1994; and Brekke et al., The Immunologist 2: 125, 1994).

In other embodiments, the chimeric polypeptide can include the mutant IL-2 polypeptide and a polypeptide that functions as an antigenic tag, such as a FLAG sequence. FLAG sequences are recognized by biotinylated, highly specific, anti-FLAG antibodies, as described herein (see also Blanar et al., Science 256:1014, 1992; LeClair et al., Proc. Natl. Acad. Sci. USA 89:8145, 1992). In some embodiments, the chimeric polypeptide further comprises a C-terminal c-myc epitope tag.

In other embodiments, the chimeric polypeptide includes the mutant IL-2 polypeptide and a heterologous polypeptide that functions to enhance expression or direct cellular localization of the mutant IL-2 polypeptide, such as the Aga2p agglutinin subunit (see, e.g., Boder and Wittrup, Nature Biotechnol. 15:553-7, 1997).

In other embodiments, a chimeric polypeptide including a mutant IL-2 and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

Nucleic Acid Molecules Encoding Mutant IL-2

In some embodiments the mutant IL-2 polypeptide, either alone or as a part of a chimeric polypeptide, such as those described above, can be obtained by expression of a nucleic acid molecule. Just as mutant IL-2 polypeptides can be described in terms of their identity with wild-type IL-2 polypeptides, the nucleic acid molecules encoding them will necessarily have a certain identity with those that encode wild-type IL-2. For example, the nucleic acid molecule encoding a mutant IL-2 polypeptide can be at least 50%, at least 65%, preferably at least 75%, more preferably at least 85%, and most preferably at least 95% (e.g., 99%) identical to the nucleic acid encoding wild-type IL-2 (e.g., SEQ ID NO:2). The nucleic acid sequence encoding mature IL-2 and its signal sequence are found in SEQ ID NO: 17.

The nucleic acid molecules provided can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Exemplary isolated nucleic acid molecules of the present disclosure can include fragments not found as such in the natural state. Thus, this disclosure encompasses recombinant molecules, such as those in which a nucleic acid sequence (for example, a sequence encoding a mutant IL-2) is incorporated into a vector (e.g., a plasmid or viral vector) or into the genome of a heterologous cell (or the genome of a homologous cell, at a position other than the natural chromosomal location).

As described above, the mutant IL-2 polypeptide of the invention may exist as a part of a chimeric polypeptide. In addition to, or in place of, the heterologous polypeptides described above, a nucleic acid molecule of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-hosphotransferase (HPH), thymidine kinase (TK), lacz (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter.

The nucleic acid molecules of the invention can be obtained by introducing a mutation into IL-2-encoding DNA obtained from any biological cell, such as the cell of a mammal. Thus, the nucleic acids of the invention (and the polypeptides they encode) can be those of a mouse, rat, guinea pig, cow, sheep, horse, pig, rabbit, monkey, baboon, dog, or cat. In one embodiment, the nucleic acid molecules will be those of a human.

Expression of Mutant IL-2 Gene Products

The nucleic acid molecules described above can be contained within a vector that is capable of directing their expression in, for example, a cell that has been transduced with the vector. Accordingly, in addition to mutant IL-2 polypeptides, expression vectors containing a nucleic acid molecule encoding a mutant IL-2 polypeptide and cells transfected with these vectors are among the preferred embodiments.

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, vectors that can be used include those that allow the DNA encoding the IL-2 muteins to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction of a Modular Dihydrafolate Reductase cDNA Gene: Analysis of Signals Utilized for Efficient Expression", Mol. Cell. Biol., 2, pp. 1304-19 (1982)) or glutamine synthetase ("GS") amplification (see, e.g., U.S. Pat. No. 5,122,464 and European published application 338,841).

In some embodiments, the human IL-2 muteins of the present disclosure will be expressed from vectors, preferably expression vectors. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of coding sequences to which they are operably linked. In general, expression vectors of utility in recombinant DNA techniques are often in the form of plasmids (vectors). However, other forms of expression vectors, such as viral vectors (e.g., replication defective retroviruses, adenoviruses, and adeno-associated viruses) are included also.

Exemplary recombinant expression vectors can include one or more regulatory sequences, selected on the basis of the host cells to be used for expression, operably linked to the nucleic acid sequence to be expressed.

The expression constructs or vectors can be designed for expression of an IL-2 mutein or variant thereof in prokaryotic or eukaryotic host cells.

Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

Expression of proteins in prokaryotes is most often carried out in *Escherichia coli* with vectors containing constitutive or inducible promoters. Strategies to maximize recombinant protein expression in *E. coli* can be found, for example, in Gottesman (1990) in Gene Expression Technology: Methods in Enzymology 185 (Academic Press, San Diego, Calif.), pp. 119-128 and Wada et al. (1992) Nucleic Acids Res. 20:2111-2118. Processes for growing, harvesting, disrupting, or extracting the IL-2 mutein or variant thereof from cells are substantially described in, for example, U.S. Pat. Nos. 4,604,377; 4,738,927; 4,656,132; 4,569,790; 4,748,234; 4,530,787; 4,572,798; 4,748,234; and 4,931,543, herein incorporated by reference in their entireties.

In some embodiments the recombinant IL-2 muteins or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast S. cerenvisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see Chapters 16 and 17 of Sambrook et al. (1989) Molecular Cloning: A Laboratory Manual ($2^{nd}$ ed., Cold Spring Harbor Laboratory Press, Plainview, N.Y.). See, Goeddel (1990) in Gene Expression Technology: Methods in Enzymology 185 (Academic Press, San Diego, Calif.).

The sequences encoding the human IL-2 muteins of the present disclosure can be optimized for expression in the host cell of interest. The G-C content of the sequence can be adjusted to levels average for a given cellular host, as calculated by reference to known genes expressed in the host cell. Methods for codon optimization are well known in the art. Codons within the IL-2 mutein coding sequence can be optimized to enhance expression in the host cell, such that about 1%, about 5%, about 10%, about 25%, about 50%, about 75%, or up to 100% of the codons within the coding sequence have been optimized for expression in a particular host cell.

Vectors suitable for use include T7-based vectors for use in bacteria (see, for example, Rosenberg et al., Gene 56:125, 1987), the pMSXND expression vector for use in mammalian cells (Lee and Nathans, J. Biol. Chem. 263:3521, 1988), and baculovirus-derived vectors (for example, the expression vector pBacPAK9 from Clontech, Palo Alto, Calif.) for use in insect cells.

In some embodiments nucleic acid inserts, which encode the polypeptide of interest in such vectors, can be operably linked to a promoter, which is selected based on, for example, the cell type in which expression is sought.

In selecting an expression control sequence, a variety of factors should also be considered. These include, for example, the relative strength of the sequence, its controllability, and its compatibility with the actual DNA sequence encoding the IL-2 mutein of this invention, particularly as regards potential secondary structures. Hosts should be selected by consideration of their compatibility with the chosen vector, the toxicity of the product coded for by the DNA sequences of this invention, their secretion characteristics, their ability to fold the polypeptides correctly, their fermentation or culture requirements, and the ease of purification of the products coded for by the DNA sequences.

Within these parameters one of skill in the art may select various vector/expression control sequence/host combinations that will express the desired DNA sequences on fermentation or in large scale animal culture, for example, using CHO cells or COS 7 cells.

The choice of expression control sequence and expression vector, in some embodiments, will depend upon the choice of host. A wide variety of expression host/vector combinations can be employed. Useful expression vectors for eukaryotic hosts, include, for example, vectors with expression control sequences from SV40, bovine papilloma virus, adenovirus and cytomegalovirus. Useful expression vectors for bacterial hosts include known bacterial plasmids, such as plasmids from E. coli, including col E1, pCRI, pER32z, pMB9 and their derivatives, wider host range plasmids, such as Rβ4, phage DNAs, e.g., the numerous derivatives of phage lambda, e.g., NM989, and other DNA phages, such as M13 and filamentous single stranded DNA phages. Useful expression vectors for yeast cells include the 2μ plasmid and derivatives thereof. Useful vectors for insect cells include pVL 941 and pFastBac™ 1 (GibcoBRL, Gaithersburg, Md.). Cate et al., "Isolation Of The Bovine And Human Genes For Mullerian Inhibiting Substance And Expression Of The Human Gene In Animal Cells", Cell, 45, pp. 685-98 (1986).

In addition, any of a wide variety of expression control sequences can be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast a-mating system, the polyhedron promoter of Baculovirus, and other sequences known to control the expression of genes of prokaryotic or eukaryotic cells or their viruses, and various combinations thereof.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance ($neo^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes a mutant IL-2 polypeptide are also features of the invention. A cell of the invention is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the invention.

The precise components of the expression system are not critical. For example, a mutant IL-2 polypeptide can be produced in a prokaryotic host, such as the bacterium E. coli, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

In some embodiments, IL-2 muteins obtained will be glycosylated or unglycosylated depending on the host organism used to produce the mutein. If bacteria are chosen as the host then the IL-2 mutein produced will be unglycosylated. Eukaryotic cells, on the other hand, will glycosylate the IL-2 muteins, although perhaps not in the same way as native-IL-2 is glycosylated. The IL-2 mutein produced by the transformed host can be purified according to any suitable method. Various methods are known for purifying IL-2. See, e.g. Current Protocols in Protein Science, Vol 2. Eds: John E. Coligan, Ben M. Dunn, Hidde L. Ploehg, David W. Speicher, Paul T. Wingfield, Unit 6.5 (Copyright 1997, John Wiley and Sons, Inc. IL-2 muteins can be isolated from inclusion bodies generated in E. coli, or from conditioned medium from either mammalian or yeast cultures producing a given mutein using cation exchange, gel filtration, and or reverse phase liquid chromatography.

Figure 2:
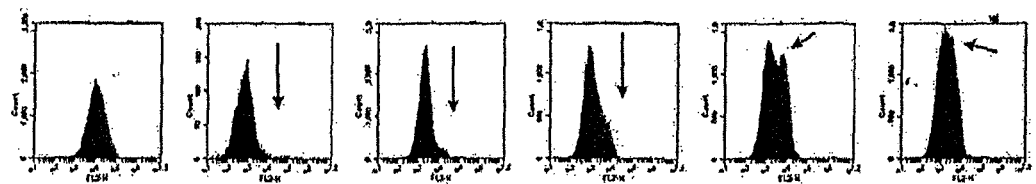
FIG. 2: FACS profile of IL-2 library. Products of error prone PCR of the human IL-2 gene were subjected to selection. The first generation IL-2 library was generated through six rounds of selection. The first round was performed using tetrameric IL-2Rβ coupled to phycoerythrin (PE) to bind yeast expressing IL-2 muteins (A). Subsequent rounds of selection were accomplished using monomeric IL-2 Rβ labeled with PE. (B) Results from the second generation IL-2 library.
Figure 2:
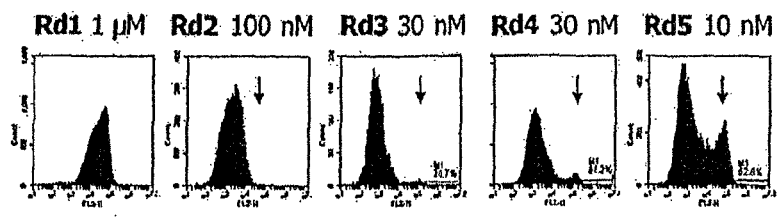

Another exemplary method of constructing a DNA sequence encoding the IL-2 muteins is by chemical synthesis. This includes direct synthesis of a peptide by chemical means of the protein sequence encoding for an IL-2 mutein exhibiting the properties described. This method can incorporate both natural and unnatural amino acids at positions that affect the interactions of IL-2 with the IL-2Rα, the IL-2Rβ and/or the IL-2Rγ. Alternatively a gene which encodes the desired IL-2 mutein can be synthesized by chemical means using an oligonucleotide synthesizer. Such oligonucleotides are designed based on the amino acid sequence of the desired IL-2 mutein, and preferably selecting those codons that are favored in the host cell in which the recombinant mutein will be produced. In this regard, it is well recognized that the genetic code is degenerate—that an amino acid may be coded for by more than one codon. For example, Phe (F) is coded for by two codons, TIC or TTT, Tyr (Y) is coded for by TAC or TAT and his (H) is coded for by CAC or CAT. Trp (W) is coded for by a single codon, TGG. Accordingly, it will be appreciated that for a given DNA sequence encoding a particular IL-2 mutein, there will be many DNA degenerate sequences that will code for that IL-2 mutein. For example, it will be appreciated that in addition to the preferred DNA sequence for mutein 5-2 shown in FIG. 2, there will be many degenerate DNA sequences that code for the IL-2 mutein shown. These degenerate DNA sequences are considered within the scope of this disclosure. Therefore, "degenerate variants thereof" in the context of this invention means all DNA sequences that code for and thereby enable expression of a particular mutein.

The biological activity of the IL-2 muteins can be assayed by any suitable method known in the art. Such assays include PHA-blast proliferation and NK cell proliferation.

Methods of Treatment

In some embodiments, mutant IL-2 polypeptides, and/or nucleic acids expressing them, can be administered to a subject to treat a disorder associated with abnormal apoptosis or a differentiative process (e.g., cellular proliferative disorders or cellular differentiative disorders, such as cancer, by, for example, producing an active or passive immunity). In the treatment of such diseases, the disclosed IL-2 muteins may possess advantageous properties, such as reduced vascular leak syndrome.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. The compositions of the present invention (e.g., mutant IL-2 polypeptides and/or the nucleic acid molecules that encode them) can also be administered to a patient who has a viral infection (e.g., AIDS or an influenza).

The mutant IL-2 polypeptides can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues.

Additional examples of proliferative disorders include hematopoietic neoplastic disorders.

Other examples of proliferative and/or differentiative disorders include skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of skin disorders include psoriasis, psoriatic arthritis, dermatitis (eczema), for example, exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia greata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

Patients amenable to treatment may also have psoriasis. The term "psoriasis" is intended to have its medical meaning, namely, a disease which afflicts primarily the skin and produces raised, thickened, scaling, nonscarring lesions. The lesions are usually sharply demarcated erythematosus papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, psoriasis vulgaris, eruptive (gluttate) psoriasis, psoriatic erythroderma, generalized pustular psoriasis (Von Zumbusch), annular pustular psoriasis, and localized pustular psoriasis.

Alternatively, or in addition to methods of direct administration to patients, in some embodiments, mutant IL-2 polypeptides can be used in ex vivo methods. For example, cells (e.g., peripheral blood lymphocytes or purified populations of lymphocytes isolated from a patient and placed or maintained in culture) can be cultured in vitro in culture medium and the contacting step can be affected by adding the IL-2 mutant to the culture medium. The culture step can include further steps in which the cells are stimulated or treated with other agents, e.g., to stimulate proliferation, or to expand a population of cells that is reactive to an antigen of interest (e.g., a cancer antigen or a viral antigen). The cells are then administered to the patient after they have been treated.

Pharmaceutical Compositions and Methods of Administration

In some embodiments, mutant IL-2 polypeptides and nucleic acids can be incorporated into compositions, including pharmaceutical compositions. Such compositions typically include the polypeptide or nucleic acid molecule and a pharmaceutically acceptable carrier.

A pharmaceutical composition is formulated to be compatible with its intended route of administration. The mutant IL-2 polypeptides of the invention may be given orally, but it is more likely that they will be administered through a parenteral route. Examples of parenteral routes of administration include, for example, intravenous, intradermal, subcutaneous, transdermal (topical), transmucosal, and rectal administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

In the event of administration by inhalation, the mutant IL-2 polypeptides, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the mutant IL-2 polypeptides or nucleic acids can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, compounds (mutant IL-2 polypeptides or nucleic acids) can also be prepared in the form of suppositories (e.g., with conventional suppository bases such as cocoa butter and other glycerides) or retention enemas for rectal delivery.

In some embodiments, compounds (mutant IL-2 polypeptides or nucleic acids) can also be administered by transfection or infection using methods known in the art, including but not limited to the methods described in McCaffrey et al. (Nature 418:6893, 2002), Xia et al. (Nature Biotechnol. 20: 1006-1010, 2002), or Putnam (Am. J. Health Syst. Pharm. 53: 151-160, 1996, erratum at Am. J. Health Syst. Pharm. 53:325, 1996).

In one embodiment, the mutant IL-2 polypeptides or nucleic acids are prepared with carriers that will protect the mutant IL-2 polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of such mutant IL-2 polypeptides or nucleic acids compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a mutant IL-2 polypeptides (i.e., an effective dosage) depends on the polypeptide selected. For instance, single dose amounts in the range of approximately 0.001 to 0.1 mg/kg of patient body weight can be administered; in some embodiments, about 0.005, 0.01, 0.05 mg/kg may be administered. In some embodiments, 600,000 IU/kg is administered (IU can be determined by a lymphocyte proliferation bioassay and is expressed in International Units (IU) as established by the World Health Organization $1^{st}$ International Standard for Interleukin-2 (human)). The dosage may be similar to, but is expected to be less than, that prescribed for PROLEUKIN®. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the mutant IL-2 polypeptides of the invention can include a single treatment or, can include a series of treatments. In one embodiment, the compositions are administered every 8 hours for five days, followed by a rest period of 2 to 14 days, e.g., 9 days, followed by an additional five days of administration every 8 hours.

The pharmaceutical compositions can be included in a container, pack, or dispenser together with instructions for administration.

EXAMPLES

The invention is further described in, and illustrated by, the following studies that serve as non-limiting examples.

Example 1

Functional Expression of IL-2 on the Surface of Yeast

Although IL-2 has been displayed on bacteriophage previously (Buchli et al., Arch. Biochem. Biophys. 339:79-84, 1997), the prior system was not amenable to directed evolution and therefore not suitable for obtaining IL-2 mutants with improved binding for subunits of the IL-2R. To overcome this, IL-2 was expressed on the surface of yeast cells. Human IL-2 DNA was cloned into yeast display vector pCT302. *Saccharomyces cerevisiae* strain EBY100 was transformed with the pCT302_IL-2 vector and grown for 3 days at 30° C. on SD-CAA plates. Individual colonies of IL-2 yeast were grown overnight at 30° C. in SD-CAA, then introduced in SGCAA for 2 days at 20° C. The yeast were stained with tetramerized biotinylated IL-2Rβ, biotinylated γ or biotinylated IL-2Rβ in the presence of biotinylated γ. The ectodomains of IL-2Rβ and γ were C-terminally biotinylated and coupled to phycoerythrin-conjugated strepavidin for use as a staining and sorting reagent. IL-2 Rβ tetramers were formed by incubating 2 μM of biotinylated IL-2Rβ with 470 nM streptavidin-phycoerythrin (SA-PE, Invitrogen) for 15 minutes on ice. These receptor "tetramers" enhanced the avidity of the low affinity monomeric ectodomain (ECD) interactions with IL-2, enabling maximal recovery of IL-2 variants from libraries. Similar to solution wild-type IL-2, yeast-displayed IL-2 bound weakly to IL-2Rβ alone, did not bind to at all to γ alone, but did bind to γ in the presence of IL-2Rβ, as evidenced by diagonal staining seen by flow cytometry (data not shown). Thus, the yeast-displayed IL-2 recapitulates the cooperative assembly of the heterodimeric receptor complex on cells seen with soluble IL-2, and is therefore suitable as a platform for library selection.

Example 2

Construction and Screening of an IL-2 Mutant Library

The first generation in vitro strategy was to create an error-prone PCR library of the entire IL-2 gene. The first generation mutant IL-2 library was constructed as follows. Wildtype human interleukin-2 (IL-2) was subjected to error-prone mutagenesis using the GeneMorph® II Random Mutagenesis kit following the manufacturer's instructions. The following primers were used for error-prone PCR: 5'-GCACCTACTTCAAGTTCTAC-3' ("IL-2_errprone_for) SEQ ID NO: 17 and 5'-GCCACCAGAGGATCC-3' ("IL-2_errprone_rev) SEQ ID NO: 18. The product of the error prone PCR reaction was then amplified using the following primers: 5'AGTGGTGGTGGTGGTTCTGGTGGTGGTG-GTTCTGGTGGTGGTTCTGCTAGCGC ACCTACT-TCAAGTTCTAC-3' SEQ ID NO: 19 and 5'ACACTGTT-GTTATCAGATCTCGAGCAAGTCTTCTTCGGAGATA-AGCTTTTGTTCGC CACCAGAGGATCC-3' SEQ ID NO: 20 to yield approximately 130 μg of DNA. Yeast display vector pCT302 was double digested with restriction enzymes NheI and BamHI and gel purified. The IL-2 DNA and the pCT302 DNA were mixed together in a 5:1 μg ratio with electrocompetent EBY100 yeast. The yeast were electroporated to facilitate entry of the library DNA into the yeast. This electroporation was repeated approximately 20 times to yield a final library size of 1×10⁸ transformants.

Selection of First Generation IL-2 Library:

The library was subjected to six rounds of selection against IL-2Rβ (FIG. 2A). In the first round, the library was labeled with 470 nM tetrameric IL-2Rβ, which was formed by mixing 2 μM biotinylated IL-2Rβ with 470 nM streptavidin-phycoerythrin conjugate (SAV-PE) for 15 min. The library was incubated with IL-2Rβ for 1.5 h, washed with PBS-BSA buffer (phosphate buffered saline+bovine serum albumin), and incubated with Miltenyi anti-PE MicroBeads for 20 min at 4° C. The cells were again washed and flowed over a magnetic column for selection. This selection method was successively repeated five more times with alterations only in IL-2Rβ concentration (round 2—1 μM, round 3—1 μM, round 4—300 nM, round 5—300 nM, round 6—100 nM, all monomeric IL-2Rβ). Upon conclusion of selections, round five and round six yeast cultures were spread on SD-CAA plates, which yielded individual yeast colonies. Eighteen resulting yeast colonies were tested for binding to 500 nM IL-2Rβ. The IL-2 DNA isolated from these eighteen yeast colonies was sequenced. Amino acid differences among these eighteen yeast colonies relative to the corresponding residue in wildtype IL-2 is shown in Table 1.

TABLE 1

| | residue # | | | | | | | | | | | | |
|---|---|---|---|---|---|---|---|---|---|---|---|---|---|
| wt IL-2 | 5 | 34 | 43 | 61 | 74 | 75 | 77 | 81 | 85 | 103 | 106 | 112 | 120 |
| | S | P | K | E | Q | S | N | R | L | F | E | A | R |
| 5_1 | | | | | R | | | | | | | | |
| 5_2 | | | | | | | | | V | | | | |
| 5_3 | | | | | | | | | V | | D | | |
| 5_4 | | | | | | K | | | | Y | | | |
| 5_5 | | | | | | | | | V | | | | |
| 5_6 | | R | | | | | | | | | | | S |
| 5_8 (wt) | | | | | | | | | | | | | |
| 5_9 | | | | | | R | | | | | | V | |
| 5_10 | | | | | | | | | V | | | | |
| 6_1 | | | | | | | | | V | | | | |
| 6_2 | | | | | R | R | | | | | | | |
| 6_3 | | | N | | | | | | V | | | | |
| 6_4 | | | | | | | | | V | | | | |
| 6_5 | | | | | | | | | V | | | | |
| 6_6 | | | | | | | | I | V | | | | |
| 6_7 | | | | | | | | I | V | | | | |
| 6_8 | | | | K | | | | | V | | | | |
| 6_10 | T | | | | | | | | V | | | | |

Library Construction of Second Generation IL-2 Library:

Based on the high percentage of clones containing L85V, a second IL-2 library was constructed that focused primarily on hydrophobic core residues. A site-directed IL-2 library was constructed with mutations at Q74, L80, R81, L85, I86, I89, I92, V93. Q74 was allowed to vary as H/K/N/Q/R/S. R81 was allowed to vary at all 20 amino acids with the NNK degenerate codon, where N represents a 25% mix each of adenine, thymine, guanine, and cytosine nucleotides and K is either guanine or thymine. The remaining residues were allowed to vary as F/I/L/V. The library was constructed by assembly PCR using the following oligos:

IL-2_affmat_ass01
                                              SEQ ID NO: 21
GCACCTACTTCAAGTTCTACAAAGAAAACACAGCTACAACTGGAGCA IL-2_affmat_ass02
                                              SEQ ID NO: 22
CAAAATCATCTGTAAATCCAGAAGTAAATGCTCCAGTTGTAGCTGTG

```
IL-2_affmat_ass03
                                             SEQ ID NO: 23
GGATTTACAGATGATTTTGAATGGAATTAATAATTACAAGAATCCCA IL-2_affmat_ass04B
                                             SEQ ID NO: 24
AACTTAGCTGTGAGCATCCTGGTGAGTTTGGGATTCTTGTAATTATT IL-2_affmat_ass05B
                                             SEQ ID NO: 25
GGATGCTCACAGCTAAGTTTTACATGCCCAAGAAGGCCACAGAACTG IL-2_affmat_ass06
                                             SEQ ID NO: 26
GTTCTTCTTCTAGACACTGAAGATGTTTCAGTTCTGTGGCCTTCTTG IL-2_affmat_ass07
                                             SEQ ID NO: 27
CAGTGTCTAGAAGAAGAACTCAAACCTCTGGAGGAAGTGCTAAATTTA IL-2_affmat_ass08
                                             SEQ ID NO: 28
GTGAAAGTTTTTGCTSYKAGCTAAATTTAGCACTTCCTCC IL-2_affmat_ass09
                                             SEQ ID NO: 29
AGCAAAAACTTTCACNTCNNKCCCAGGGACNTCNTCAGCAATNTCAACG

TANTCNTCCTGGAACTAAAGGGATC

IL-2_affmat_ass10
                                             SEQ ID NO: 30
CATCAGCATATTCACACATGAATGTTGTTTCAGATCCCTTTAGTTCCAG IL-2_affmat_ass11
                                             SEQ ID NO: 31
ATGTGTGAATATGCTGATGAGACAGCAACCATTGTAGAATTTCTGAACA IL-2_affmat_ass12
                                             SEQ ID NO: 32
AGATGATGCTTTGACAAAAGGTAATCCATCTGTTCAGAAATTCTACAAT IL-2_affmat_ass13
                                             SEQ ID NO: 33
TTTTGTCAAAGCATCATCTCAACACTAACTGGATCCTCTGGTGGC
```

The site-directed PCR was amplified with the following oligos:
PCR Amplification Oligos (Including 50 bp Homology)

```
IL-2_site2_assFor:
                                             SEQ ID NO: 34
5'-AGTGGTGGTGGTGGTTCTGGTGGTGGTGGTTCTGGTGGTGGTGGTTCTGCTAGCGCACC

TACTTCAAGTTCTAC-3'

IL-2_site2_assRev:
                                             SEQ ID NO: 35
5'-ACACTGTTGTTATCAGATCTCGAGCAAGTCTTCTTCGGAGATAAGCTTTTGTTCGCCACCA

GAGGATCC-3'
```

The PCT yielded 40 μg of DNA, which was mixed with double digested pCT302 and electrocompetent EBY100 yeast and electroporated as with the first generation library.
Selection of Second Generation IL-2 Library:

The library was subjected to five rounds of selection against IL-2Rβ (FIG. 2B). This selection method was performed exactly as with the first generation library, only with modifications to the concentrations of IL-2Rβ used (round 1—1 μM, round 2—100 nM, round 3—30 nM, round 4—30 nM, round 5—10 nM, all monomeric IL-2Rβ). Upon conclusion of selections, round four and round five yeast cultures were spread on SD-CAA plates, which yielded individual yeast colonies. 48 individual yeast clones from both rounds were grown in 96-well block format and screened by labeling with 5 nM IL-2Rβ and then SAV-PE. The screen yielded seven high affinity binders to IL-2Rβ. Amino acid differences among these seven high affinity binders relative to the corresponding residue in wildtype IL-2 is shown in Table 2 along with the binding affinity for IL-2Rβ.

TABLE 2

| residue # | 74 | 80 | 81 | 85 | 86 | 89 | 92 | 93 | $K_d$ (nM) |
|---|---|---|---|---|---|---|---|---|---|
| wt IL-2 | Q | L | R | L | I | I | I | V | 280 |
| B1 | N | F | D | V | V | V | | F | 1.6 |
| C5 | N | V | T | V | V | | | F | 10 |
| D10 | H | F | D | V | V | | | F | 1.2 |
| E10 | S | F | D | V | V | | | F | 1.3 |
| G8 | N | F | D | V | V | | | F | 1.5 |
| H4 | S | | | T | V | | | F | 14 |
| H9 | | F | D | V | V | | | F | 1.3 |
| CONSENSUS | | F | D | V | V | | | F | |

Example 3

IL-2 Mutein Protein Expression and Purification

Human IL-2 variants (amino acids 1-133), the IL-2Rβ ectodomain (amino acids 1-214), and γ$_c$ (amino acids 34-232) were cloned into the pAcGP67-A vector (BD Biosciences) in frame with an N-terminal gp67 signal sequence and C-terminal hexahistidine tag and produced using the baculovirus expression system. Baculovirus stocks were prepared by transfection and amplification in *Spodoptera frugiperda* (Sf9) cells grown in SF900II media (Invitrogen), and protein expression was carried out in suspension *Trichoplusia ni* (High Five™) cells grown in BioWhittaker® Insect XPRESS™ media (Lonza). Proteins were expressed and captured from High Five™ supernatants after 48-60 hr by nickel agarose (QIAGEN), concentrated and purified by size exclusion chromatography on a Superdex™ 200 column (GE Healthcare), equilibrated in 10 mM HEPES (pH 7.2) and 150 mM NaCl. IL-2 variants used in SPR and cell based assays were expressed fully glycosylated. For biotinylated receptor expression, IL-2Rβ and γ$_c$ were cloned into the pAcGP67-A vector with a C-terminal biotin acceptor peptide (BAP)-LNDIFEAQKIEWHE SEQ ID NO: 36 and hexahistidine tag. Receptor proteins were coexpressed with BirA ligase with excess biotin (100 uM).

Example 4

Stimulation of CD25⁻ and CD25⁺ Natural Killer (YT-1) Cells

YT-1 and CD25+ YT-1 cells were cultured in RPMI 1640 medium supplemented with 10% fetal bovine serum, 2 mM L-glutamine, minimum non-essential amino acids, sodium pyruvate, 25 mM HEPES, and penicillin-streptomycin (Gibco). CD25⁺ YT-1 cells were purified as follows: $1\times10^7$ cells were washed with FACS buffer (phosphate buffered saline+2% bovine serum albumin) and stained with PE-conjugated anti-human CD25 (1:20; Biolegend, San Diego, Calif.) in 1 mL FACS buffer for 20 minutes at 4° C. The stained cells were labeled with paramagnetic microbeads coupled to anti-PE IgG and separated with an LS MACS® separation column according to the manufacturer's instructions (Miltenyi Biotec, Bergisch Gladbach, Germany). Eluted cells were re-suspended in complete RPMI medium at a concentration of $1\times10^5$ cells and expanded for subsequent experiments. Enrichment of cells was monitored via flow cytometry with the FL-2 channel using an Accuri® C6 flow cytometer.

Figure 4:
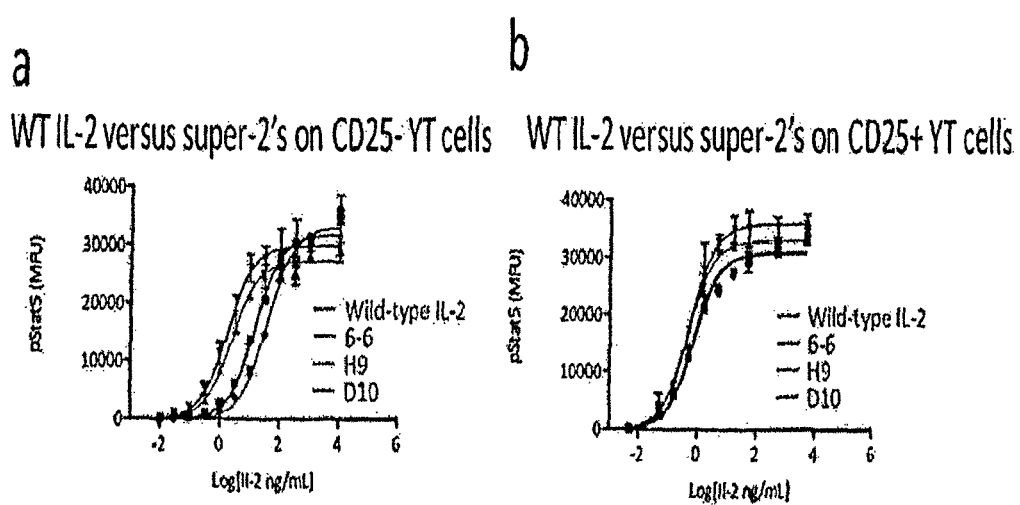
FIG. 4: Stimulatory Effects of IL-2 Muteins on CD25⁻ and CD25⁺ Natural Killer Cells. Dose response relationships of wildtype IL-2 and the IL-2 muteins 6-6, D10, and H9 on STAT5 phosphorylation witnessed in treated (A) CD25⁻ and (B) CD25⁺ YT-1 Natural Killer cells. Circles wild-type IL-2; squares 6-6; triangles up H9; triangles down D10.

The dose-response relationships of H9, D10, and 6-6 on YT-1 cells was determined by assaying STAT5 phosphorylation with flow cytometry (FIGS. 4a and 4b). CD25⁺ or CD25⁻ YT-1 cells were washed with FACS buffer and re-suspended in 200 μL FACS buffer with the indicated concentration of wild-type, 6-6, H9, or D10 in a 96 well plate. Cells were stimulated for 20 minutes at room temperature and then fixed by addition of formaldehyde to 1.5% and incubated for 10 min. Cells were permeabilized with 100% ice-cold methanol for 20 min on ice, followed by incubation at −80° C. overnight. Fixed, permeabilized cells were washed with excess FACS buffer and incubated with 50 μL Alexa647 conjugated anti-STAT5 pY694 (BD Biosciences, San Jose, Calif.) diluted 1:20 in FACS buffer for 20 minutes. Cells were washed twice in FACS buffer and mean cell fluorescence determined using the FL-4 channel of an Accuri® C6 flow cytometer.

Figure 5:
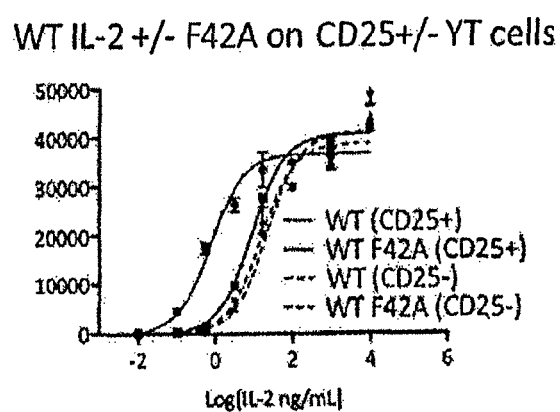
FIG. 5: CD25 Independence of IL-2 Mutein Binding. Dose response curves of STAT5 phosphorylation for CD25⁻ and CD25⁺ YT-1 Natural Killer cells. (A) IL-2 and IL-2 (F42A) (circles, solid line wild-type IL-2, CD25+ cells; squares, solid line IL-2 F42A, CD25+ cells; triangles up, dashed lines wild-type IL-2, CD25− cells; triangles down, dashed line, IL-2 F42A, CD25− cells). (B) H9 and H9(F42A) (circles, solid line wild-type H9, CD25+ cells; squares, solid line H9 F42A, CD25+ cells; triangles up, dashed lines H9, CD25− cells; triangles down, dashed line, H9 F42A, CD25− cells). While the F42A mutation right shifted the dose-response curve of wild-type IL-2 on CD25⁺ cells, but had no observable effect on CD25⁻, the dose response curves for H9 and H9 F42A were essentially overlapping, regardless of CD25 expression.
Figure 5:
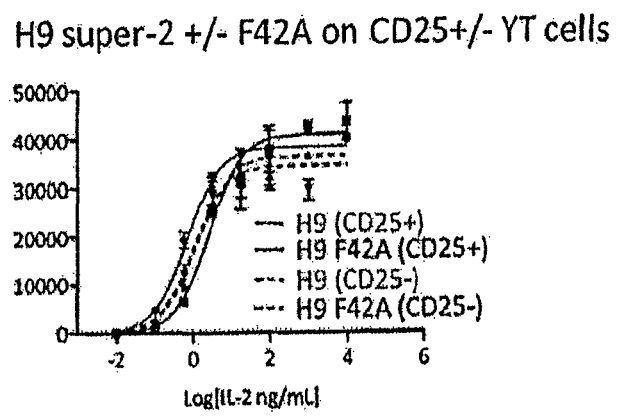

The CD25 independence of the IL-2 muteins (so called "super-2" molecules) was further tested by taking advantage of a well-characterized mutation of IL-2, phenylalanine to alanine at position 42 (F42A), which abolishes binding to CD25, yet does not effect its ability to bind to the IL-2Rβ or the IL-2Rγ (Mott, 1995). This mutation was also introduced into the H9 mutein, yielding H9 F42A. A comparison of STAT induction by IL-2, IL-2 F42A, H9 and H9 F42A on CD25− and CD25+ YT-1 cells was performed (FIG. 5). While IL-2 F42A mutation right shifted the dose response curve of wild-type IL-2 on CD25+ cells by approximately 1 log, the F42A mutation had no observable effect on STAT induction on CD25− cells (FIG. 5a). In contrast, the dose response curves of H9 and H9 F42A were essentially overlapping on both CD25− and CD25+ cells. Thus, these experiments demonstrate that while the IL-2 muteins do not apparently benefit from the presence of CD25, their activity is insensitive to mutations that disrupt the CD25 interface.

Example 5

Stimulation of CD25− and CD25+ T cells

Human and mouse CD4 T cells were prepared from PBMC (Stanford Blood Bank) and spleens and lymph nodes of BALB/C mice, respectively using antibody-coated CD4 T cell isolation magnetic beads (Stem Cell Technologies and Miltenyi Biotec). For nave cell stimulation assays, cells were used immediately. For generation of in vitro 'experienced' T cells, wells were pre-coated with secondary antibody (Vector Labs) in bicarbonate buffer, pH 9.6 prior to coating plates with anti-CD3 (OKT3 for human, 2C11 for mouse, eBiosciences) at 100 ng/mL. T cells were seeded at $0.1\times10^6$ cells/well with soluble anti-CD28 (CD28.2 for human, 37.51 for mouse, eBiosciences). Cell were cultured for 3 days with full TCR stimulated, followed by 2 days rest in conditioned media and 2 days rest in fresh culture media. Prior to use, live cells were collected by Lympholyte-M (Cederlane) centrifugation and counted.

Figure 6:
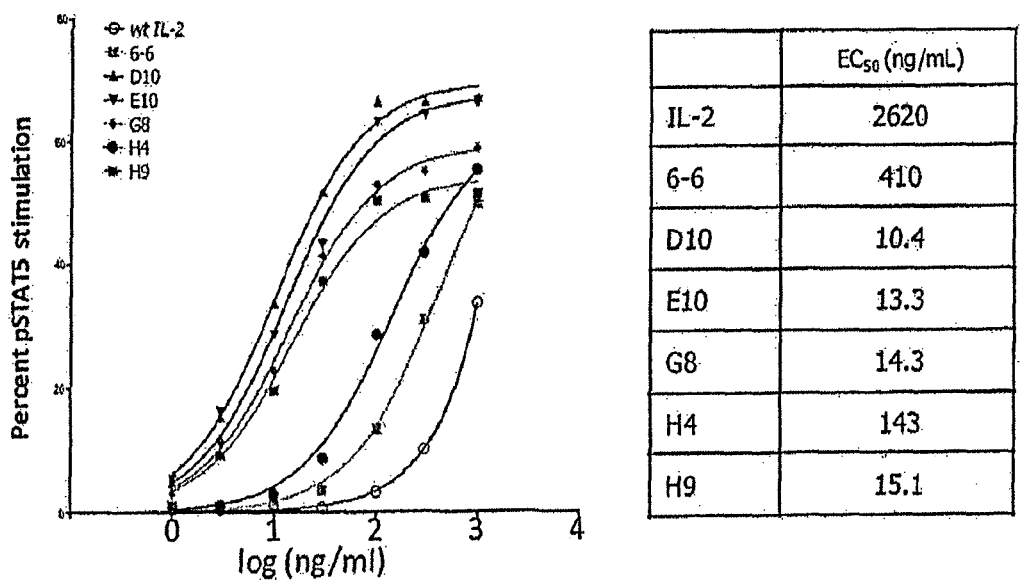
FIG. 6: CD25 KO T cell stimulation. The ability of the disclosed IL-2 muteins to stimulate T cells in the absence of the IL-2Rα was tested. T cells isolated from CD25 knockout mice were stimulated with an IL-2 mutein or wild-type IL-2. Dose response curves and respective EC50 of IL-2 muteins are provided. As shown, all of the tested IL-2 muteins resulted in relatively increased T cell stimulation, in the absence of the IL-2Rα, relative to wild-type IL-2.

The activity of IL-2 muteins on T cells that were either deficient in CD25 expression or expressed CD25 was assessed (FIG. 6). The dose response relationship of wild-type IL-2 and six IL-2 muteins were assayed for STAT5 phosphorylation at a protein concentration range of 1 ng/ml to 1000 ng/ml. The ability of the IL-2 muteins to stimulate STAT5 phosphorylation in CD25 deficient T cells correlated well with their affinity for the IL-2Rβ. The increase in STAT5 phosphorylation by the IL-2 muteins was two orders of magnitude greater that IL-2.

Figure 7:
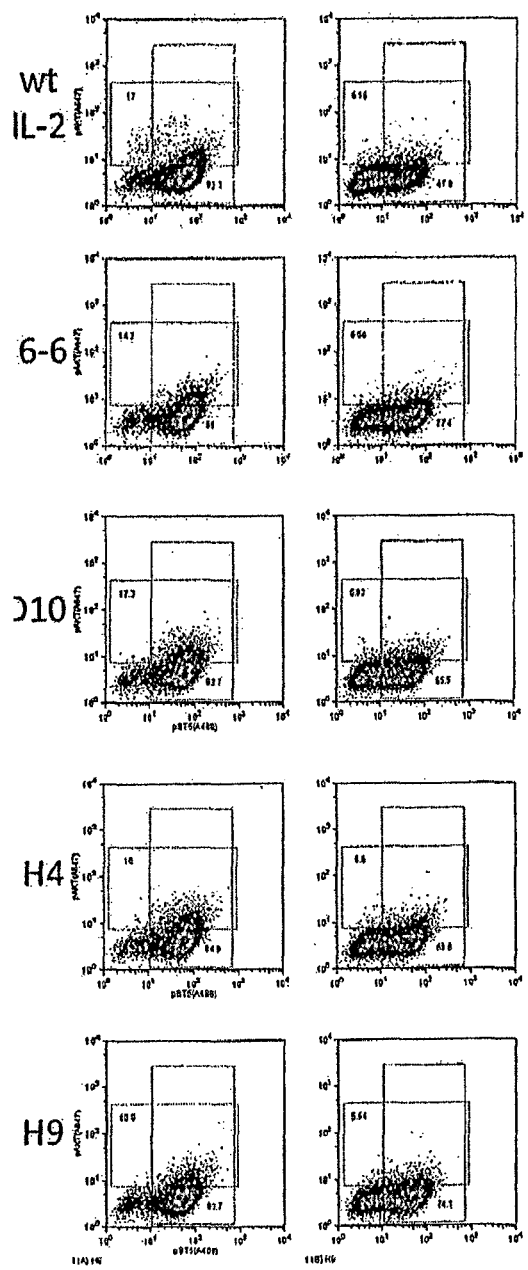
FIG. 7: Human experienced CD4 T cell stimulation. FACS analysis comparing the relative ability of the disclosed IL-2 muteins to induce experienced T cell stimulation. T cells were stimulated with two concentrations (10 ng/ml or 1 ng/ml) of IL-2 mutein or wild-type IL-2. The percentage of stimulated T cells is shown in each FACS profile.

The ability of IL-2 muteins to stimulate STAT5 phosphorylation on experienced human CD4+ T cells, which express large amounts of the full IL-2 receptor complex, CD25 (IL-2Rα), IL-2β, and $\gamma_c$ was also assessed (FIG. 7). Human CD4 T cells were in vitro TCR stimulated and rested to generate 'experienced' human CD4+ CD25+ T lymphocytes. At 1 ng/mL, almost no difference in STAT5 phosphorylation was observed. Each IL-2 variant, including wild-type, stimulated over 90% of the cells. At 0.1 ng/mL, small differences were observed. Wildtype IL-2 resulted in 48% pSTAT5 stimulation, and the IL-2 muteins yielded between 65-79% pSTAT5 stimulation. Therefore, the IL-2 muteins apparently stimulate experienced human T cells better than wildtype IL-2 but the enhancement is not as pronounced as on cells lacking CD25

Example 6

NK Cell Cytotoxicity Assay

The effect of the D10 IL-2 mutein on Natural Killer cell function, specifically spontaneous and antibody-dependent cell-mediated cytotoxicity (ADCC) using an EGFR (endothelial growth factor receptor)-expressing squamous tumor cell line (SCC6) and the EGFR monoclonal antibody, cetuximab was assessed. Human EGFR-positive squamous cell carcinoma cell line, SCC6, was obtained as a gift from the J. Sunwoo Laboratory (Stanford, Calif.). SCC6 cell line was cultured in DMEM/F12 medium (Invitrogen Life Technologies) supplemented with 10% heat-inactivated FCS (HyClone Laboratories), 100 U/mL penicillin and 100 μg/mL streptomycin (both from Invitrogen Life Technologies). Cells were grown adherent in culture at 37° C. in 5% $CO_2$. Cetuximab (mouse chimeric IgG1 anti-human epidermal growth factor receptor-EGFR; IMC-C225; Erbitux®) was obtained from Bristol-Myers Squibb.

Figure 8:
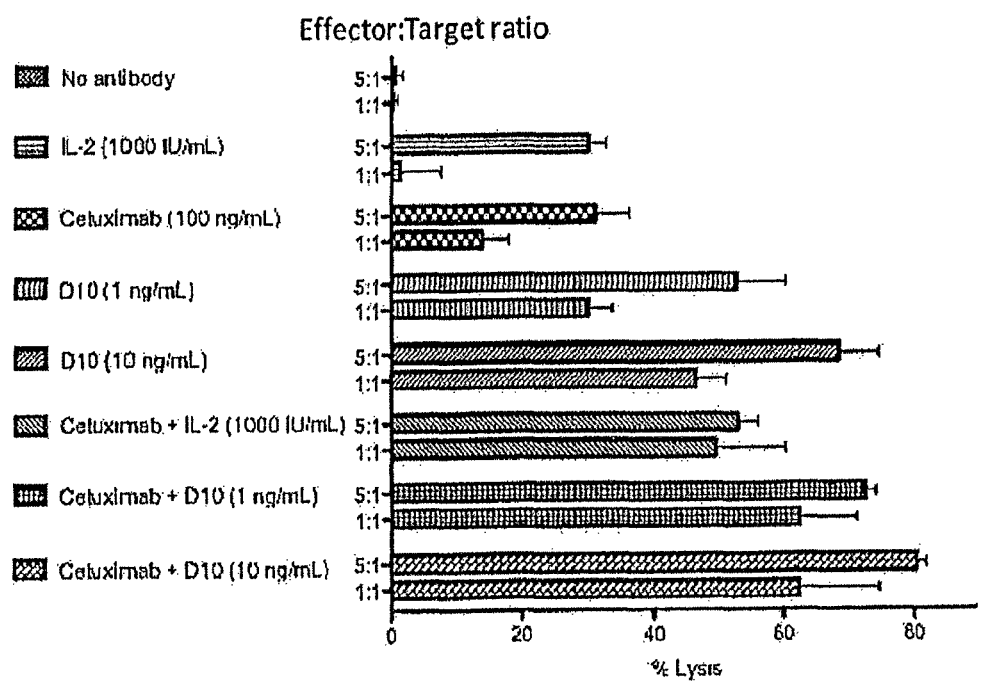
FIG. 8: Antibody dependent cellular cytotoxity (ADCC). The effect of IL-2 mutein D10 on natural killer cell function, specifically spontaneous and antibody-dependent cell mediated cytotoxicity was assayed. Natural killer cells (effectors) and $Cr^{51}$ labeled tumor cells (targets) were incubated together for 5 hours in the presence of wild-type IL-2 or the IL-2 mutein D10, with or without the anti-EGFR antibody cetuximab. D10 stimulation of NK cell spontaneous cytotoxicity was superior to high dose IL-2 (*p=0.008, **p=0.001) with minimal spontaneous cytotoxicity without IL-2 or D10 stimulation. Further, addition of D10 enhanced the ADCC of the cetuximab antibody.

Chromium release was performed as follows: NK cells were isolated from a healthy donor leukocyte-reduced system (LRS) product containing approximately $1\times10^9$ cells. NK cells were isolated by negative magnetic cell sorting using NK cell isolation beads (Miltenyi Biotec) according to manufacturer's instructions. NK cells were assessed for purity (>90% purity as defined by CD3⁻ CD56⁺ flow cytometry). SCC6 target cells were labeled with 150 μCi ⁵¹Cr per $1\times10^6$ cells for 2 h. Percent lysis was determined after 5 h cultures of purified NK cells at variable effector:target cell ratios of 0:1, 1:1, and 5:1 with $^{51}$Cr-labeled SCC6 cells in media alone, cetuximab (100 pg/mL), IL-2 (1000 IU/mL), IL-2 D10 (1 pg/mL), IL-2 D10 (10 pg/mL), or combinations including cetuximab (100 pg/mL) plus IL-2(1000 IU/mL), cetuximab (100 pg/mL) plus IL-2 D10 (1 pg/mL), or cetuximab (100 pg/mL) plus IL-2 D10 (10 pg/mL). Assay was performed in triplicate. Purified NK cells were cultured with $^{51}$Cr labelled-SCC6 cells in the presence or absence of cetuximab, IL-2 or IL-2 D10 at variable concentrations. D10 stimulation of NK cell spontaneous cytotoxicity was superior to high-dose IL-2 (FIG. 8, *p=0.008, **p=0.001) with minimal spontaneous cytotoxicity without IL-2 or D10 stimulation. ADCC of cetuximab-bound SCC6 was similarly increased by D10 stimulation compared to high-dose IL-2 or cetuximab alone (*p=0.0005, **p=0.0001). Notably, superior functional enhancement of cytotoxicity, both spontaneous and ADCC, occurred at all effector:target ratios including 1:1 with D10 compared to high-dose IL-2.

Example 7

IL-2 Muteins Result in Enhanced Memory Phenotype Expansion with Relatively Low Stimulation of Suppressor-Type T Cells (Tregs)

Figure 10:
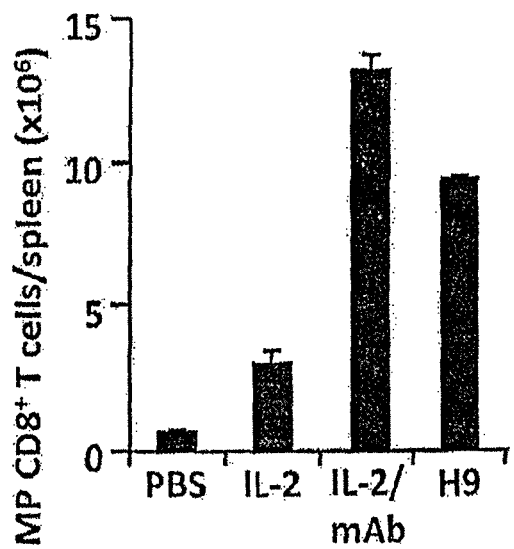
FIG. 10: Novel IL-2 muteins exhibit enhanced stimulation of CD8⁺ T cells but not Tregs relative to IL-2. (A) Total cell counts of host $CD3^+$ $CD8^+$ $CD44^{high}$ memory-phenotype (MP) T cells and (B) host $CD3^+$ $CD4^+$ $CD25^{high}$ T cells (regulatory T cells) was determined in the spleens of mice receiving either PBS, 20 μg IL-2, 20 μg H9, or 1.5 μg IL-2/anti-IL-2 monoclonal antibody complexes (IL-2/mAb).
Figure 10:
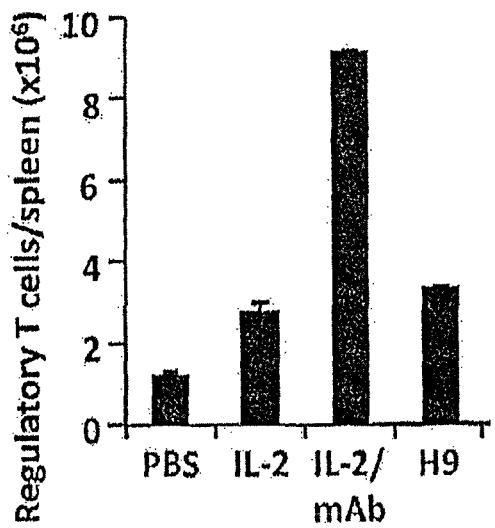

The potency of the IL-2 mutein H9 on the expansion of memory phenotype CD8$^+$ T cells expressing low levels of CD25 but high levels of IL-2Rγ was assessed in vivo. C57Bl/6 mice received either PBS, 20 μg IL-2, 20 μg H9, or 1.5 μg IL-2/anti-IL-2 monoclonal antibody complexes and total cell counts of splenic CD3$^+$ CD4$^+$ CD44$^{high}$ memory phenotype T cells were assessed by flow cytometry. Splenic cell suspensions were prepared and stained with fluorochrome-conjugated monoclonal antibodies CD3 (clone 145-2C11, eBioscience), CD4 (clone RM4-5, Caltag Laboratories), CD8a (clone 53-6.7, BD Biosciences), CD25 (clone PC61, BD Biosciences), CD44 (clone IM7, eBioscience) NK1.1 (clone PK136, BD Biosciences) and Thy1.1 (clone HIS51, eBioscience). At least 100,000 viable cells were acquired using a BD FACSCanto™ II flow cytometer and analyzed using FlowJo software (TriStar, Inc.). As shown in FIG. 10(A), treatment with the disclosed IL-2 mutein resulted in greater expansion of memory phenotype T cells relative to other treatment modalities with limited expansion of CD3$^+$ CD4$^+$ CD25$^{high}$ T cells regulatory T cells FIG. 10(B).

Example 8

Reduced In Vivo Toxicity of IL-2 Muteins

Figure 11:
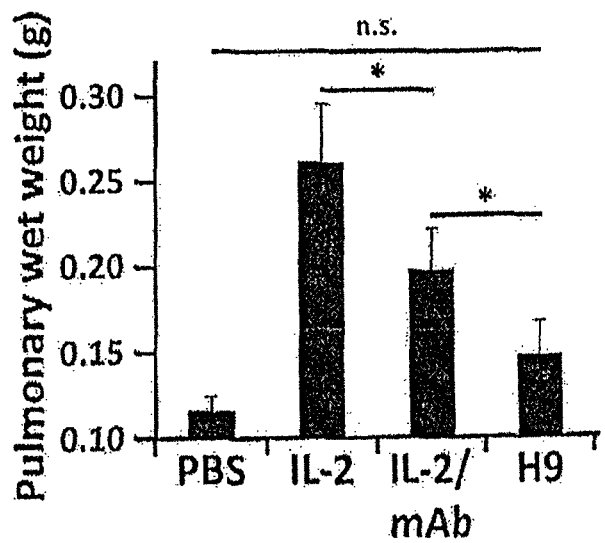
FIG. 11: Novel IL-2 muteins exhibit enhanced anti-tumor response with reduced adverse effects relative to IL-2. Pulmonary edema (pulmonary wet weight) served as a measure of adverse toxic effects following IL-2 treatment, and was determined by weighing the lungs before and after drying (A). P values refer to comparisons between treatment modalities. *, p<0.05; **, p<0.01. (B) Anti-tumor properties of IL-2 muteins were tested in vivo using B16F10 melanoma cells. C57Bl/6 mice (n=3-4 mice/group) were injected subcutaneously with 106 B16F10 melanoma cells followed by daily injections of either PBS, 20 μg IL-2, 20 μg H9, or 1.5 μg IL-2/anti-IL-2 monoclonal antibody complexes (IL-2/mAb) for five days once tumor nodules became visible and palpable, which typically corresponded to day 4 to 5 after tumor cell injections or a tumor size of about 15 $mm^2$. Shown is mean tumor area in $mm^2$ (+/−SD) vs. time upon tumor inoculation. P values refer to comparison of IL-2 with the other treatment modalities.
Figure 11:
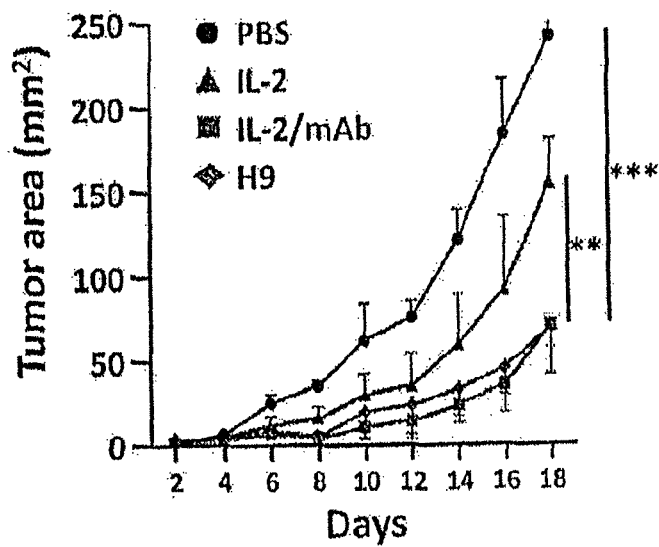

It is known that IL-2 treatment can lead to severe adverse effects, such as acute pulmonary edema, which is currently a limitation preventing more effective use of IL-2. Accordingly, the toxicity of the disclosed IL-2 muteins relative to IL-2 was assessed (FIG. 11A). C57Bl/6 mice received daily intraperitoneal injections of PBS, 20 μg IL-2, 20 μg H9, or 1.5 μg IL-2/anti-IL-2 monoclonal antibody complexes for 5 consecutive days. 6 days after adoptive cell transfer, the lungs were removed and weighed before and after drying overnight at 58° C. under vacuum. Pulmonary wet weight was calculated by subtracting initial pulmonary weight from lung weight after dehydration.

Example 9

Increased Anti-Tumor Activity of IL-2 Muteins In Vivo

The potency of the disclosed IL-2 muteins against tumor cells was tested in vivo. 10$^6$ B16F10 melanoma cells in 100 μl RPMI were injected into the upper dermis in the back of mice (3-4 mice per group). Treatment consisted of five daily injections of either PBS, 20 μg IL-2, 20 μg H19, or 1.5 μg IL-2/anti-IL-2 monoclonal antibody complexes (IL-2/mAb) and was started one day after tumor nodules were clearly visible and palpable at a size of ~15 mm$^2$. The disclosed IL-2 mutein resulted in enhanced anti-tumor activity in vivo as demonstrated in FIG. 11(B).

Example 10

Structural Comparison of IL-2 Muteins and IL-2

Several of the IL-2 muteins were recombinantly expressed in order to measure their binding affinity and kinetics for IL-2Rβ by surface plasmon resonance (SPR). The affinity between IL-2 and IL-2Rβ was $K_D$=280 nM. The IL-2 muteins clustered into low, medium, and high affinity classes. The low affinity IL-2 muteins (5-2 and 6-6) bound IL-2Rβ with $K_D$ between 50 and 70 nM, respectively, an affinity gain of 4-6 fold from wild-type IL-2 almost entirely through the L85V substitution. The medium and high affinity mutants selected from the secondary, site-directed library had $K_D$'s of 10-15 nM (C5, H4), and 1.2-1.7 nM (B1, D10, E10, G8, H9), respectively. The affinity increases were uniformly manifested in reductions in off-rate, and the high affinity IL-2 muteins contained a consensus sequence in the randomized positions of L80F/R81D/L85V/I86V/I92F.

Figure 9:
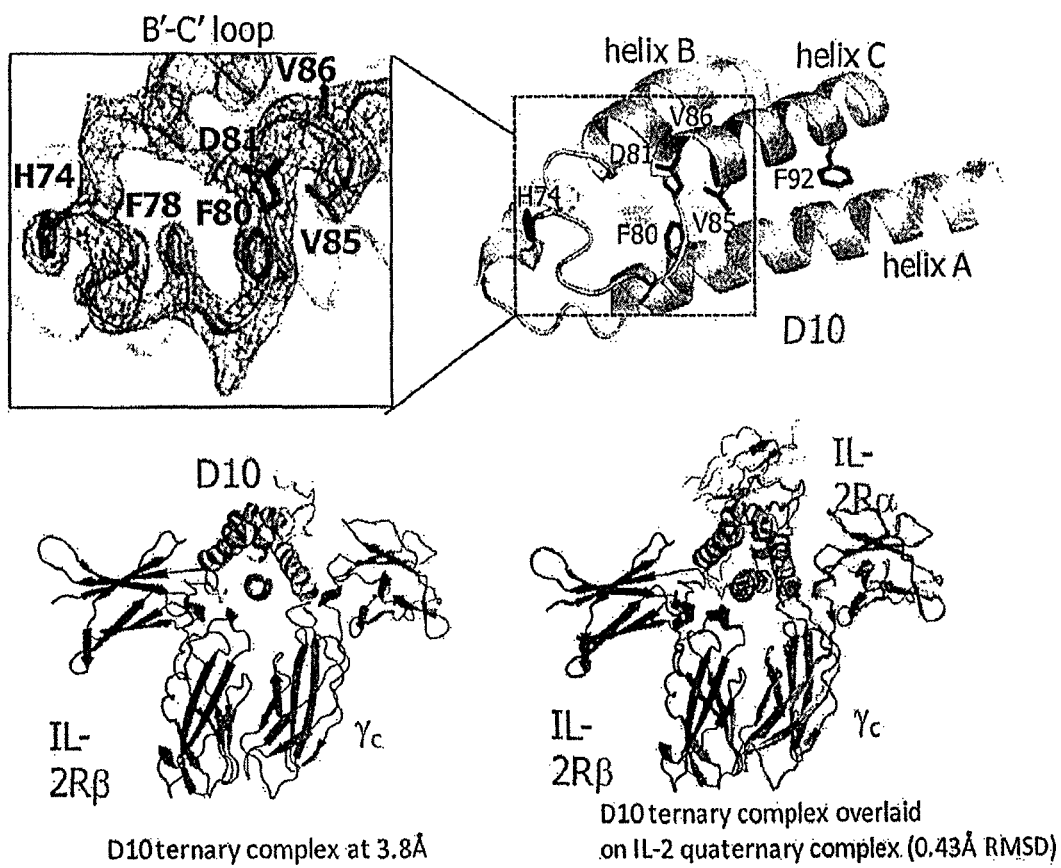
FIG. 9: Crystal structure of D10. An initial hydrophobic core mutation of L85V led to a second generation IL-2 library targeting multiple hydrophobic core residues and a high affinity consensus sequence. The crystal structure of D10 contained well-defined electron density in the loop region preceding helix C.

To understand the structural consequences of the IL-2 muteins, the D10 mutein as well as the ternary complex of D10 bound to IL-2Rβ and γ$_c$ were crystallized. In the structure of D10 alone, five of the six mutations are clustered on the B-C loop and within the C helix core, in positions that do not contact IL-2Rβ. Notably, the B-C helix linker region is well-ordered in the electron density map (FIG. 9), compared to other IL-2 structures where this region is either partially or completely disordered. Collectively, the F80, V85, and V86 substitutions appear to collapse into a hydrophobic cluster that stabilizes the loop and 'pins' the C-helix into the core of the molecule, packing against helix B. The 1-174 and D81 mutations are solvent exposed and thus, their structural roles are less clear, however Asp is a well-known helix N-capping residue that could further contribute the helix C structure. Only one of the six consensus mutations, I92F, was at a position that contacts IL-2Rβ in the receptor complex. Phe92 is deeply inserted between the C and A helices, contributing only an additional 10 Å$^2$ of molecular surface buried by IL-2Rβ in the complex compared to Ile92. Thus, its IL-2Rβ contact likely makes only a small contribution to the overall ~300-fold affinity gain of D10.

A low-resolution (3.8 Å) structure of the D10 ternary receptor complex was also determined to assess whether the mutations have perturbed the IL-2Rβ/γc receptor docking geometry. A stable ternary complex of D10 and IL-2Rβ, was crystallized and purified in the absence of CD25. The overall IL-2Rβ/γc heterodimeric architecture and mode of cytokine/IL-2Rβ contact in the D10 ternary complex is essentially identical to the previously reported quaternary assembly. Thus, the potency increase of super-2 is not due to a structural change in receptor dimer architecture, but is likely due to the affinity enhancement.

As discussed earlier, the C-helix of IL-2 appears to undergo subtle repositioning upon binding to IL-2Rα, as seen in both the binary and quaternary complexes. In contrast, inspection of three wild-type unliganded structures in the PDB database reveals variability in the C-helix position, consistent with higher B-factors in this helix relative to the rest of the molecule. Comparison of the structure of D10 to that of an unliganded IL-2, and IL-2 in the receptor complexes was undertaken. It was observed that the C-helix in D10 is more similar to that seen in the two receptor-bound conformations of IL-2 than the free forms, having undergone a shift up and into the helical core.

Molecular dynamics (MD) simulations were used to interrogate the mechanism by which an IL-2 mutein is endowed with higher binding affinity for IL-2Rβ. An atomically detailed Markov state model (MSM) was constructed in order to directly probe the relative conformational flexibility of IL-2 versus IL-2 muteins. The states in this MSM come from kinetic clustering of rapidly inter-converting conformations resulting from atomistic simulations. Each of these metastable states corresponds to a local minimum in the underlying free energy landscape that ultimately determines the systems' structure and dynamics. Analysis of the MSM demonstrates that an IL-2 mutein can be more stable than IL-2, and that IL-2 visits nearly twice as many clusters as an IL-2 mutein. For example, IL-2 muteins most populated state has an equilibrium probability of ~0.20, compared to ~0.05 for IL-2. Helix B, the B-C loop, and helix C are rigidified in the IL-2 mutein compared to IL-2. As the evolved mutations reside on the B-C loop (H74, D81), and within the B and C helix packing interface (F80, V85, V86), both helices—not just helix C—benefit from the mutations and undergo a collective stabilization. F92 appears to act as a molecular wedge between helix C and helix A, acting as an additional stabilizing influence at the more C-terminal end of the helix. That the MD simulations implicate helix B as also undergoing stabilization in super-2 was a surprise, since this was not evident from comparison of IL-2 crystal structures. IL-2Rα binds to IL-2 primarily on the B helix and part of the D helix. The MD simulations suggest the possibility that binding of IL-2Rα to IL-2 may rigidify helix B, and this structural stabilization may be propagated to the B-C loop and helix C. Similar, in principle, to the apparent effect of the evolved mutations in the IL-2 mutein.

Visualization of the most highly populated conformations from the simulations for each protein shows that helix C, is far more flexible in IL-2 than the IL-2 mutein, and also that the mutations in the IL-2 mutein do indeed stabilize a receptor-bound-like conformation.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, although IL-2 is referred to throughout the specification, one of skill in the art would appreciate that the methods and compositions described herein are equally applicable to other cytokines, for example, granulocyte-macrophage colony-stimulating factor (GM-CSF), IL-2, IL-3, IL-5, IL-6, or IL-15 with this property. Thus, the invention also includes mutants of GM-CSF, IL-2, IL-3, IL-5, IL-6, and IL-15 with increased binding affinity for their respective receptors, as compared to wild-type, and methods for identifying and using those mutants.

We claim:

1. An interleukin-2 receptor β (IL-2Rβ) binding protein, wherein the equilibrium dissociation constant for the IL-2Rβ of said binding protein is less than that of wild-type human IL-2 (hIL-2), and wherein said IL-2Rβ binding protein comprises the following amino acid substitutions: L80F, R81D, L85V, I86V, and I92F, numbered in accordance with wild-type hIL-2.

2. The binding protein of claim 1, wherein the binding protein further comprises one or more amino acid substitutions at positions selected from the group consisting of I24, F42, K43, P65, Q74, I89, and V93.

3. The binding protein of claim 1, wherein the binding protein further comprises one or more amino acid substitutions at positions selected from the group consisting of F42 and K43.

4. The binding protein of claim 1, wherein the binding protein further comprises the following amino acid substitution: K43N.

5. The binding protein of claim 1, wherein the binding protein further comprises the following amino acid substitution: F42A.

6. The binding protein of claim 1, wherein the binding protein comprises the following substitutions: F42A, L80F, R81D, L85V, I86V, I89V, and I92F.

7. The binding protein of claim 1, wherein the binding protein further comprises one or more amino acid substitutions selected from the group consisting of I24V, P65H, Q74R, Q74H, Q74N, Q74S, I89V, and V93I.

8. The binding protein of claim 7, wherein the binding protein comprises the following amino acid substitution: Q74N.

9. The binding protein of claim 1, wherein the binding protein comprises the following substitutions: Q74N, L80F, R81D, L85V, I86V, I89V, and I92F.

10. The binding protein of claim 1, wherein the binding protein comprises the following substitutions: L80F, R81D, L85V, I86V, I89V, I92F, and V93I.

11. The binding protein of claim 1, wherein the binding protein comprises the following substitutions: Q74H, L80F, R81D, L85V, I86V, and I92F.

12. The binding protein of claim 1, wherein the binding protein comprises the following substitutions: Q74S, L80F, R81D, L85V, I86V, and I92F.

13. The binding protein of claim 1, wherein the binding protein comprises the following substitutions: Q74N, L80F, R81D, L85V, I86V, and I92F.

14. The binding protein of claim 3, which exhibits reduced binding to an IL-2Rα relative to wild-type IL-2.

15. The binding protein of claim 1, wherein the binding protein comprises the following substitutions: T18R, P22E, L80F, R81D, L85V, I86V, I89V, I92F, V93I, and E126T.

16. The binding protein of claim 15, wherein said binding protein inhibits interaction between IL-2Rβ and IL-2Rγ.

17. The binding protein of claim 15, which exhibits reduced binding to IL-2Rγ relative to wild-type IL-2.

18. The binding protein of claim 15, which exhibits reduced signaling through IL-2Rγ relative to wild-type IL-2.

* * * * *